United States Patent
Roholt et al.

(10) Patent No.: US 10,702,375 B2
(45) Date of Patent: Jul. 7, 2020

(54) ELECTROMYOGRAPHIC SENSING AND VISION MODIFICATION

(71) Applicant: Vista Ocular, LLC, N. Canton, OH (US)

(72) Inventors: Philip C. Roholt, Canton, OH (US); William Kokonaski, Gig Harbor, WA (US); Jean-Noël Fehr, Neuchâtel (CH); Randolph McDonald, San Anselmo, CA (US)

(73) Assignee: VISTA OCULAR, LLC, N. Canton, OH (US)

( * ) Notice: Subject to any disclaimer, the term of this patent is extended or adjusted under 35 U.S.C. 154(b) by 344 days.

(21) Appl. No.: 15/268,566

(22) Filed: Sep. 17, 2016

(65) Prior Publication Data

US 2017/0079771 A1    Mar. 23, 2017

Related U.S. Application Data

(60) Provisional application No. 62/359,277, filed on Jul. 7, 2016, provisional application No. 62/279,407, filed
(Continued)

(51) Int. Cl.
*A61F 2/16*    (2006.01)
*G02C 7/08*    (2006.01)
(Continued)

(52) U.S. Cl.
CPC .......... *A61F 2/1635* (2013.01); *A61B 5/0492* (2013.01); *A61B 5/686* (2013.01);
(Continued)

(58) Field of Classification Search
CPC ................. A61F 2/1635; A61F 2/1624; A61F 2002/1683; A61F 2002/482; A61F 2250/0002; G02C 7/04; G02C 7/083
See application file for complete search history.

(56) References Cited

U.S. PATENT DOCUMENTS

| 4,373,218 A | 2/1983 | Schachar |
| 4,585,457 A | 4/1986 | Kalb |

(Continued)

FOREIGN PATENT DOCUMENTS

| DE | 10155345 A1 | 5/2003 |
| EP | 2687898 A1 | 1/2014 |

OTHER PUBLICATIONS

DeLuca, Carlos J., Surface Electromyography: Detection and Recording. Delsys, Inc, 2002.
(Continued)

*Primary Examiner* — David H Willse
*Assistant Examiner* — Tiffany P Shipmon
(74) *Attorney, Agent, or Firm* — Grasso PLLC

(57) ABSTRACT

Adjustable vision modification using various systems, devices, and processes are provided. Adjustable vision modification may include sensing ocular related physiological activities of a user and making adjustments in an ocular device or ocular system to change the vision of the user. Various sensors and sensor locations may be employed in embodiments to sense or otherwise obtain these physiological activities. Likewise, various ocular devices, ocular processes, and ocular systems may be employed for improving vision.

19 Claims, 26 Drawing Sheets

Related U.S. Application Data on Jan. 15, 2016, provisional application No. 62/264,151, filed on Dec. 7, 2015, provisional application No. 62/254,850, filed on Nov. 13, 2015, provisional application No. 62/245,661, filed on Oct. 23, 2015, provisional application No. 62/220,756, filed on Sep. 18, 2015.

(51) Int. Cl.
*G02C 7/04* (2006.01)
*A61B 5/00* (2006.01)
*A61B 5/0492* (2006.01)
*A61F 2/48* (2006.01)

(52) U.S. Cl.
CPC .............. *A61B 5/6821* (2013.01); *G02C 7/04* (2013.01); *G02C 7/083* (2013.01); *A61F 2002/1683* (2013.01); *A61F 2002/482* (2013.01); *A61F 2220/0025* (2013.01); *A61F 2250/0002* (2013.01)

(56) References Cited

U.S. PATENT DOCUMENTS

| | | |
|---|---|---|
| 4,816,031 A | 3/1989 | Pfoff |
| 5,108,429 A | 4/1992 | Wiley |
| 5,171,266 A | 12/1992 | Wiley et al. |
| 5,203,788 A | 4/1993 | Wiley |
| 5,800,530 A | 9/1998 | Rizzo, III |
| 6,096,078 A | 8/2000 | McDonald |
| 6,120,538 A | 9/2000 | Rizzo, III et al. |
| 6,511,508 B1 | 1/2003 | Shahinpoor et al. |
| 6,618,208 B1 | 9/2003 | Silver |
| 6,797,004 B1 | 9/2004 | Brady et al. |
| 7,041,133 B1 | 5/2006 | Azar |
| 7,060,094 B2 | 6/2006 | Shahinpoor et al. |
| 7,118,596 B2 | 10/2006 | Zadno-Azizi et al. |
| 7,198,640 B2 | 4/2007 | Nguyen |
| 7,238,201 B2 | 7/2007 | Portnry et al. |
| 7,261,736 B1 | 8/2007 | Azar |
| 7,309,943 B2 | 12/2007 | Henderson et al. |
| 7,326,246 B2 | 2/2008 | Brady et al. |
| 7,334,892 B2 | 2/2008 | Goodall et al. |
| 7,390,088 B2 | 6/2008 | Goodall |
| 7,416,562 B2 | 8/2008 | Gross |
| 7,486,988 B2 | 2/2009 | Goodall et al. |
| 7,591,849 B2 | 9/2009 | Richardson |
| 7,795,782 B2 | 9/2010 | Wischnewskij et al. |
| 7,857,850 B2 | 12/2010 | Mentak et al. |
| 7,941,201 B2 | 5/2011 | Chiou |
| 7,964,833 B2 | 6/2011 | Holladay |
| 8,425,599 B2 | 4/2013 | Shadduck |
| 8,574,295 B2 | 11/2013 | Roholt |
| 8,778,002 B2 | 7/2014 | Blum |
| 8,900,298 B2 | 12/2014 | Anvar et al. |
| 8,919,953 B1 | 12/2014 | Ho |
| 8,968,396 B2 | 3/2015 | Matthews et al. |
| 9,036,264 B2 | 5/2015 | Gupta et al. |
| 9,052,528 B2 | 6/2015 | Pugh |
| 9,084,561 B2 | 7/2015 | Etzkorn |
| 9,084,673 B2 | 7/2015 | Dell |
| 9,111,473 B1 | 8/2015 | Ho |
| 9,113,829 B2 | 8/2015 | Etzkorn |
| 9,125,736 B2 | 9/2015 | Kahook et al. |
| 9,155,614 B2 | 10/2015 | Blum et al. |
| 9,220,590 B2 | 12/2015 | Beer |
| 9,277,987 B2 | 3/2016 | Smiley et al. |
| 9,364,318 B2 | 6/2016 | Beer |
| 9,456,895 B2 | 10/2016 | Shadduck |
| 2004/0148022 A1 | 7/2004 | Eggleston |
| 2005/0256571 A1* | 11/2005 | Azar ............... A61F 2/1613 623/6.22 |
| 2006/0122530 A1 | 6/2006 | Goodall et al. |
| 2006/0122531 A1 | 6/2006 | Goodall et al. |
| 2006/0136055 A1 | 6/2006 | Michel |
| 2007/0005136 A1 | 1/2007 | Richardson |
| 2007/0142909 A1 | 6/2007 | Peyman |
| 2008/0021549 A1* | 1/2008 | Eagan ............... A61F 2/1616 623/6.22 |
| 2008/0177170 A1 | 7/2008 | Roberts et al. |
| 2010/0331974 A1 | 12/2010 | Schaper, Jr. |
| 2010/0331977 A1 | 12/2010 | Schaper, Jr. |
| 2011/0040378 A1 | 2/2011 | Werblin |
| 2011/0177393 A1 | 7/2011 | Park et al. |
| 2012/0046744 A1 | 2/2012 | Woods et al. |
| 2013/0184815 A1* | 7/2013 | Roholt ............... A61F 2/1635 623/6.22 |
| 2013/0261744 A1 | 10/2013 | Gupta et al. |
| 2014/0156000 A1 | 6/2014 | Campin |
| 2014/0227437 A1 | 8/2014 | DeBoer et al. |
| 2015/0173893 A1 | 6/2015 | Portney |

OTHER PUBLICATIONS

Mettingvanrijn, A.C, et al., Low-cost Active Electrode Improves the Resolution in Biopotential Recordings, Academic Medical Center, Medical Physics Department, Meibergdreef 15 1105 AZ Amsterdam, The Netherlands, Oct.-Nov. 1996.

Marques, E.F., et al. Clinical Performance of a New Aspheric Dual-Optic Accommodating Intraocular Lens, Dove Press Journal, Clin Ophthalmology, Nov. 19, 2014.

Bausch + Lomb, Crystalens Advanced Optics (AO) Accommodating IOL, www.bausch.com.

Karavitaki, AE, at al. Long-term Visual Outcomes after Crystalens HD introcular lens implantation, Clinical Opthomology, May 22, 2014.

Larkin, Howard, Dual-Optic IOL, Eurotimes, vol. 16; Issue 5, 2011.

U-M Kellogg Eye Center, Kellogg Resident Creates New Intraocular Power Source, www.kellogg.umich.edu, 2014.

EW Supplement: Crystalens AO: Outstanding Vision Quality Across a More Natural Range; ASCRS—EyeWorld, Mar. 2012.

PCT/US2013/021663 International Publication No. WO 2013/109579, with ISR, published Jul. 25, 2013 (28 pages).

EP Application 13738060.6 European Patent Office Communication, with extended European Search Report, dated Jun. 8, 2015 (7 pages).

PCT/F12009/050622 International Publication No. WO 2010/004094, with ISR, published Jan. 14, 2010 (28 pages).

EP 13 73 8060, Search Opinion & Supplementary EP Search Report, dated May 28, 2015.

PCT/US2013/021663, International Preliminary Report on Patentability, dated Jul. 22, 2014.

PCT/US2013/021663, International Search Report, dated Apr. 25, 2013.

WO 2010/004094 A1, Published Jan. 14, 2010, with ISR (28 pages).

PCT/US2016/052400, International Search Report & Written Opinion, dated Dec. 29, 2016 (12 pages).

J. James Saladin, et al., Impedance Cyclography as an Indicator of Ciliary Muscle Contraction, American Journal of Optometry and Physiological Physics, vol. 51 Sep. 1974.

Supplementary European Search Report, Application No. 16847518.4-1122/3349648, dated Apr. 30, 2019.

* cited by examiner

ELECTROMYOGRAPHIC SENSING AND VISION MODIFICATION

CROSS-REFERENCE TO RELATED CO-PENDING APPLICATIONS

This application claims the benefit of and priority to the following provisional applications. First, this application claims the benefit of and claims priority to U.S. provisional application 62/220,756, which was filed on Sep. 18, 2015, and is entitled Electromyographic Sensing. This application also claims the benefit of and claims priority to U.S. provisional application 62/245,661, which was filed on Oct. 23, 2015, and is entitled Accommodating Intra-Ocular Lens System. This application also claims the benefit of and claims priority to U.S. provisional application 62/254,850, which was filed Nov. 13, 2015, and is entitled Presbyopia Treatment. This application also claims the benefit of and claims priority to U.S. provisional application 62/264,151, which was filed Dec. 7, 2015, and is entitled Opthalmic Accommodation Sensor. This application also claims the benefit of and claims priority to U.S. provisional application 62/279,407, which was filed Jan. 15, 2016, and is entitled Haptic Sensors and Detachable Components for Electro-Active Intraocular Lenses. Lastly, this application claims the benefit of and claims priority to U.S. provisional application 62/359,277, which was filed Jul. 7, 2016, and is entitled Electronic IO CM Sensor.

TECHNICAL FIELD

The present invention generally relates to vision modification, and more particularly to active ocular systems, devices, and processes for modification or correction of presbyopia or other vision impairments.

BACKGROUND

The human eye possesses natural accommodation capability. This capability involves relaxation and constriction of the circular ciliary muscle of the eye and related zonules controlled by the ciliary muscle. This relaxation and constriction, controlled by the brain, provides the eye with near and distant vision. This ciliary muscle action is automatic, and varies the shape of the natural crystalline lens to an appropriate optical configuration for focusing light rays entering the eye on the retina. Ciliary muscle relaxation, which is the normal state of the muscle, shapes the human crystalline lens for distant vision. Ciliary muscle contraction deforms the lens for near vision, and the extent of contraction changes the focal length of the lens to the desired endpoint. This change in effective focal length in order to focus on nearby objects is known as accommodation.

Normally the human eye loses its ability to accommodate as individuals reach the age of 40. This condition, known as presbyopia, is typically due to a progressive loss in the elasticity of the lens of the eye, such that the ciliary muscle can no longer exert the necessary deformation of the lens' shape. In addition, the human eye is susceptible to disorders and diseases which attack the crystalline lens, such as cataracts. Cataracts causing partial or complete blindness are typically treated by removing the crystalline lens and replacing it with an intra-ocular lens (IOL).

The conventional solution to the problem of presbyopia is a prescription for reading glasses or, for individuals who already require glasses to correct other refractive errors such as myopia or astigmatism, a prescription of bifocal or multifocal glasses. These fixed variance glasses are provided for the subject's eye to have better vision of objects at different distances.

BRIEF SUMMARY

Adjustable vision modification using various systems, devices, and processes are provided in embodiments herein. Adjustable vision modification may include sensing ocular related physiological activities of a user and making adjustments in an ocular device or ocular system to treat presbyopia of the user or otherwise change the vision of the user. Various sensors and sensor locations may be employed in embodiments to sense or otherwise obtain these physiological activities. These sensors may also be tuned, shielded, directionally positioned, and otherwise situated and adjusted to improve performance in embodiments. Also, various ocular devices, ocular processes, and ocular systems may be employed for improving vision, including treating presbyopia. These devices and systems may be implanted partially or completely within the user and may also be positioned outside of the user while, regardless of location, may be serving to improve the vision of the user. Related processes may also be employed.

Various features, steps, processes, components, and subcomponents as may be employed in embodiments are provided herein. These features, steps, processes, components, subcomponents, partial steps, systems, devices, etc. may be adjusted, combined and modified in various fashions and various ways among and between the teachings and figures provided herein, as well as in other ways not specifically described herein but consistent with the teachings and discussion of this disclosure.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION

Figure 1:
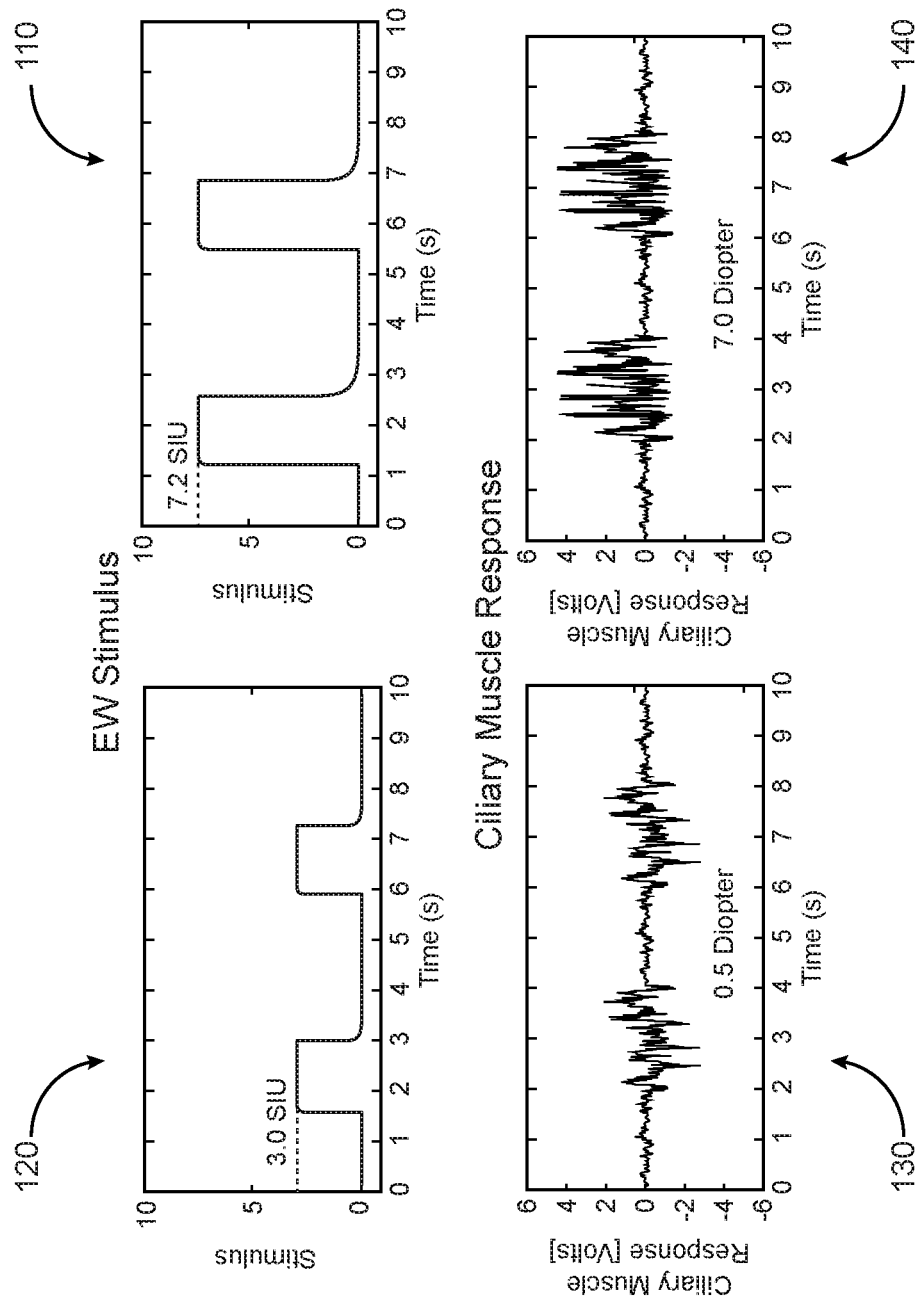
FIG. 1 is a chart showing examples of measured Rhesus monkey ciliary muscle action potential as induced by Edinger-Westphal stimulus and associated ciliary muscle dioptric response as may be employed in embodiments.

Embodiments may include devices, systems, processes, and articles of manufacture relating to adjustable vision correction. This vision correction may include active near vision accommodation as well as other vision correction or modification objectives. Embodiments may include the use of electromyogram sensing, and/or ciliary muscle impedance driving and sensing as part of a system or process to actively produce near vision accommodation in one or both eyes of a user. These systems and devices may be implanted surgically in the user, be employed in external devices or systems for the user, and in combination hybrids of these as well. These external systems and devices may include: contact lenses; eyewear; and other vision adjustment devices or systems. The vision modification may be for improving vision impaired by presbyopia as well as for other reasons, and the vision modification may comprise use of variable aperture optics and variable focus optics as well as adaptive focus optics or other vision modifications or corrections and combinations thereof.

Embodiments may harness the physiology of visual pathways of vision accommodation. This physiology may include near focus reflex following cortical stimulation and then propagation from the ciliary ganglion to the ciliary muscle. In embodiments, muscle action potential providing for muscle movement may be measured by electromyogram techniques and may be employed. Embodiments may sense in various positions along pathways of visual accommodation. These sensing positions can include the ciliary ganglion, the ciliary muscle, the medial rectus muscle, the lateral rectus muscle, the optic nerve, the oculomotor nerve, the superior colliculus, the pretectal area, the lateral geniculate nucleus, and the visual cortex. In embodiments, the pathways between and among these positions may be sensed as well.

Active devices and systems for improving vision impaired by presbyopia or other vision impairments can include correction through the use of intraocular lenses (IOLs). These lenses may be electrically activated and may consider various methods to adjust and improve presbyopia or other vision impairments. In embodiments, electromyographic sensing may be performed in order to enable active accommodations directed to improve the vision of a patient.

Embodiments may provide improved accommodative intraocular lenses (IOLs) and/or IOL systems that utilize electro-active materials in the form of a ring-shaped electrostrictive/piezoelectric actuator/motor to cause a change in shape or other characteristic of the IOL so as to facilitate accommodation in response to signals created by contraction and relaxation of the eye's ciliary muscle. Other IOL configurations and sensing techniques are also provided for in embodiments. These sensing techniques include haptic sensors with haptic electrodes positioned along deformable extensions integrated with an implantable IOL As defined herein, the term "ciliary muscle" means a ring of striated smooth muscle encircling the eye that controls accommodation for viewing objects at varying distances. The ciliary muscle also regulates the flow of aqueous humor into Schlemm's canal, through its attachment to the posterior trabecular meshwork and has parasympathetic and sympathetic innervation. The terms "ciliary body" and "ciliary complex" are structures that include the ciliary muscle.

The term "ciliary muscle signal" means an action detected at or from the subject's ciliary muscle, and more specifically means an action relating to the ciliary muscle in the form of a neuro-electrical pulsation or a muscle action potential. The ciliary muscle signal can be electrical/neuroelectrical or chemical/neurochemical in nature, and is associated with mechanical movement of the ciliary muscle.

Embodiments may provide systems and methods that allow for enhanced capacity for accommodation of implanted IOLs. Embodiments may function through detection of an electrical signal, such as an action potential created by the ciliary muscle and may act to mimic the force of contraction created by the ciliary muscle onto a native lens, and to convert this signal to activate an element formed from an electro-active polymer (EAP), thereby causing an accommodating shape change in an implanted IOL or other accommodative device. Embodiments may also provide accommodative forces in various applications, including where an EAP is in the form of one or more rings implanted around the lens of the eye. Embodiments may also provide for detection or capture of the action of the ciliary muscle and transfer of it with enough force to cause adequate IOL deformation or other change and associated accommodation.

Embodiments may include various devices, systems, and processes for vision enhancement. This vision enhancement may include correction of presbyopia as well as other near vision problems. Embodiments may include one or more electromyogram (EMG) sensors, application specific integrated circuits (ASIC), a power source such as a battery or motion conversion power system, and variable optics. In embodiments EMG sensors may sense and subsequently provide signals to be used for making adjustments to the variable optics and enhancing the vision of a user. These EMG sensors may be located at various positions, including: the intra-capsular bag, the ciliary sulcus, subconjunctival/episcleral, intrascleral, suprachoroidal, infrachoroidal/intra-vitreal, or within a contact lens, and accommodation may be located at an electro-active IOL, contact lens, spectacles, or corneal inlay. The sensors may be positioned and oriented in various ways. This positioning and orientation may be done for various reasons including summation or correction of signals received. Tuning may also be possible as well as directional adjustments and orientations of sensors and their positioning. This tuning and/or adjustments may serve to enhance, amplify, correct or otherwise improve or change sensor signals. In embodiments one or more EMG sensors may be located on foldable haptics as well as casing for filtering. These foldable haptics may include an open-ended sulcus ring or other extension that may comprise nitinol for flexibility and may be coupled to a power source and ASIC circuitry. These or other components may be placed at the eye of a user and may have the ASIC coupled to a removable lens that may have a variable aperture optic such as a liquid crystal, flexible optic, or an electrochemical lens as well as other configurations and combinations thereof.

In embodiments, an enhanced capacity for accommodation of implanted IOLs may be provided. It can be beneficial to detect a signal, such as an action potential, created by the ciliary muscle and to convert this signal to activate subsequent components and devices that achieve accommodation through optical means. An IOL (or other optical device, such as a contact lens or spectacles) can be configured to be coupled to a sensor, such as an electromyographic (EMG) receiver (or series of EMG receivers), that detects a signal created by the ciliary muscle around the eye. A receiver may then transmit the signal to a signal processor (ASIC) that may have been programmed to respond to the action potential (AP). This processing can include fast onset, sustained contraction, and muscular relaxation (disaccommodation).

Embodiments may also be configured such that output of an ASIC or other processor is transferred to the optical end-components (whether, e.g.: IOL, corneal inlay, CL, or spectacles) to effect accommodation, thereby acting as the trigger for the accommodative system. The ciliary muscle signal can be in the form of a neuro-electrical impulse, the aforementioned muscle AP, but it can also be a muscle contractile force, a chemical signal, or a combination of these means.

Embodiments may comprise one or more electromyogram ("EMG") sensors along with management circuitry (e.g., ASIC circuitry), a power supply (e.g., a battery), a communication device (e.g., wired or rf transceiver), and variable optics. Sensors in embodiments may measure the muscle action potential by measuring low brain stimulus signals at various positions or pathways of the visual pathway of accommodation. In some instances, the pathway may be the nerve from the ciliary ganglion, in which case a nerve excitatory potential may be used or otherwise considered for purposes of accommodation or other vision correction using the systems, methods, and devices taught herein. In embodiments the measurements may be used to determine an intended ciliary diopter response, which may in turn be used for making adjustments in a variable optic. This variable optic may be implanted in the patient as well as worn by the patient.

Embodiments may use microtechnology, including piezoelectric and electro-active polymers, to convert signals created by the ciliary muscle into contractile forces acting on an implanted IOL. Embodiments may also result in implantability, exceptional optical characteristics, high accommodative range, and excellent natural controllability of refractive effect by accommodative effort and resistance to the natural fibrotic and proliferative forces of the healing capsular bag and intra-capsular epithelium.

Electronic intraocular lenses in embodiments may be situated within the native capsular bag. Embodiments may also include use of ciliary muscle (CM) action potential sensors for electro-active intraocular lenses (EA-IOL). In embodiments, a CM action potential sensor may receive muscle action potential (electrical) signals, and these signals may be transferred to the Application Specific Integrated Circuit (ASIC) or other processor for further processing in conjunction with filtering signals from interfering adjacent muscles (e.g., iris sphincter, extraocular, eyelid) or elsewhere along with filters for radiofrequency interference so that the signal may be modulated for triggering the accommodative function of the optical portion of a synthetic IOL such as an EA-IOL.

Embodiments may also use a sensor to detect impedance or electrical resistance changes of the ciliary muscle. Similar to the action potential sensor, these sensors may also be most preferably positioned in close proximity to the CM. In embodiments, sensors may, preferably, be implanted as a plurality of driving and sensing pairs on a ciliary sulcus ring device or the haptic of an EA-IOL. Other configurations are also possible.

In addition to implantation of CM sensors of various types, which are often implanted inside the eye (intraocular), embodiments may employ a sensor system, which may be implanted in the suprachoroidal space, intrascleral, or episcleral in the subconjunctival space.

CM sensors may be employed through use of a separate CM sensor via a ciliary sulcus ring, and the sensor may be positioned in various locations. In addition, the CM sensors may be incorporated into the haptic of an EA-IOL, with wired or wireless connection to the EA-IOL or other vision correction device. In addition, as centration may be integral to the performance of an EA-IOL in embodiments, embodiments may preferably incorporate design modifications into the IOL to assure centration within the capsular bag.

Sensor configurations and systems employed in embodiments may have various configurations. An impedance sensor system may be employed in embodiments and may have paired electrodes consisting of a driver electrode and a sensing electrode, preferably with at least two pairs. In a preferred embodiment alternating driver and sensor electrodes may be positioned on a ring or other symmetrical shape located in the ciliary sulcus however, other positions may also be used. Companion sensors may also be implanted in episcleral, scleral, supra- or infrachoroidal within the vitreous cavity adjacent to the ciliary muscle, approximately 1-5 mm posterior to the corneal limbus. These sensors may communicate to the other components of the impedance sensor system via tuned radiofrequency. Other communication techniques may also be used.

In embodiments, sensors may be used to sense electrical activity as generated by a change in the impedance, or resistance, of the ciliary muscle when accommodation is invoked. These sensors or other components may be used as input for a control circuit that controls an adjustable focus lens used to correct or alter the focus of a human eye. In embodiments driving current may be between 0.001 and 0.3 milliamperes with a frequency of 0.1 kHz to 100 kHz to drive the system and systems may use several paired drivers and sensors. The sensors may be configured and positioned as micro- or multi-electrode arrays (MEA) and may be located within 1 mm or 3 mm of the ciliary muscle. Other positions are also plausible. In embodiments one or more of the sensors may be located in the capsular bag as well as in the ciliary sulcus, the suprachoroidal space, the infrachoroidal/vitreous cavity, and the episcleral space or intrascleral.

In embodiments, vision correction may be performed by one or more of an electroactive intra-ocular lens, an electroactive corneal inlay, an electro-active contact lens, electro-active spectacles, and combinations thereof. Power may be provided by an inductively charged battery for power as well as other techniques and wired and wireless communication systems may be employed for components and sub-components to communicate with each other.

Various other sensors may also be employed in embodiments. These sensors may include sensors associated with an accommodating IOL or other vision correction system and may be sized for insertion in the body or use outside the body. Embodiments may also be configured to monitor glucose levels, blood pressure or fluid pressure or other pressure, biochemistry markers, and electrophysiology markers.

In the case of wireless connection to the EA-IOL or other vision adjustment device, sensors may need to transmit signals to a receiver in the EA-IOL or other device. In embodiments, this may include an amplification and transmission of the raw electromyogram (EMG) signal, or may include the necessary electronics to process and filter competing signals and then transmit only a command for an accommodative response of a specific magnitude or a binary command to simply apply a fixed amount of optical power change to aid the patient in accommodation. In either case, a power source may preferably be included in the CM sensor. A small battery, an electrochemical cell, an eco drive or other electro-mechanical conversion process, thermal electric or other means to power the electronics used with or in association with the CM sensor may be employed in embodiments.

In embodiments, the native crystalline lens may be replaced by an intraocular lens, or as discussed herein, an EA-IOL. The capsule surrounds the native cataractous or non-cataract lens material in certain embodiments. A capsulorhexis is the circular opening made in the capsule of the native crystalline lens. The opening diameter is usually 5-7 mm (such as 5 mm-7 mm, 5.25 mm-6.75 mm, 5.5 mm-6.5 mm, or 5.75 mm-6 mm) in diameter. Typically, the capsulorhexis is made manually by tearing the capsule in a circular fashion. This enables the lens material, whether cataractous or not, to subsequently be removed after the anterior capsulorhexis is completed. When the opening is performed with a femtosecond laser, it is termed "capsulotomy." A capsulotomy could also be performed with radiofrequency thermal discharge, or other cutting modality.

In embodiments, it may be preferable if the electromyogram (EMG) electrode sensors, which may be used to measure the action potential of the ciliary muscle as well as impedance or resistive changes in the ciliary muscle, are affixed to the haptics of the IOL. These haptics may preferably be positioned within the capsular bag, and, having a certain amount of external force (in the amount of 0.1 to 1.5 grams of compressive force) would stretch the capsular bag so that the haptics would be in close proximity to the ciliary sulcus and the surface of the ciliary muscle.

Figure 27:
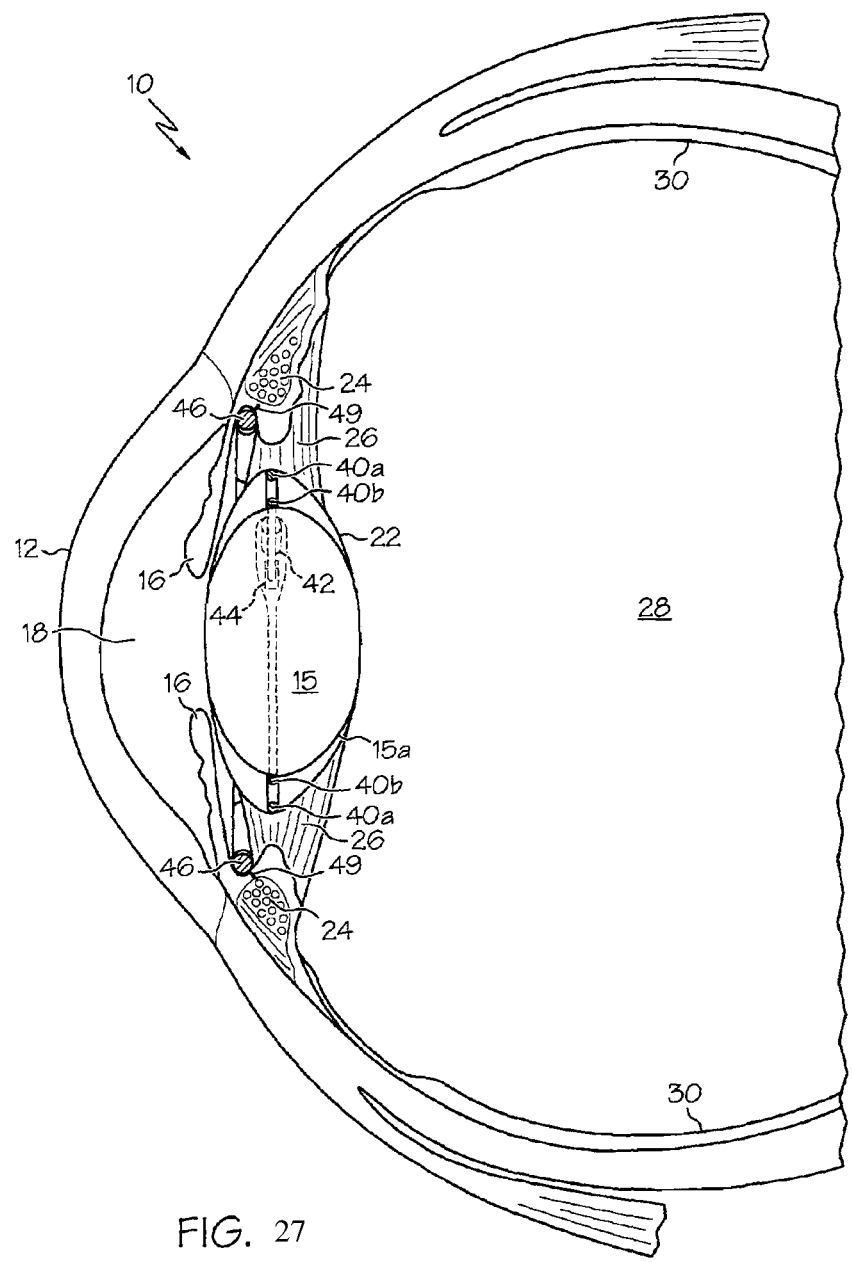
FIG. 27 is a side view illustrating the system of FIG. 25 positioned within the eye as may be employed in embodiments.
Figure 28:
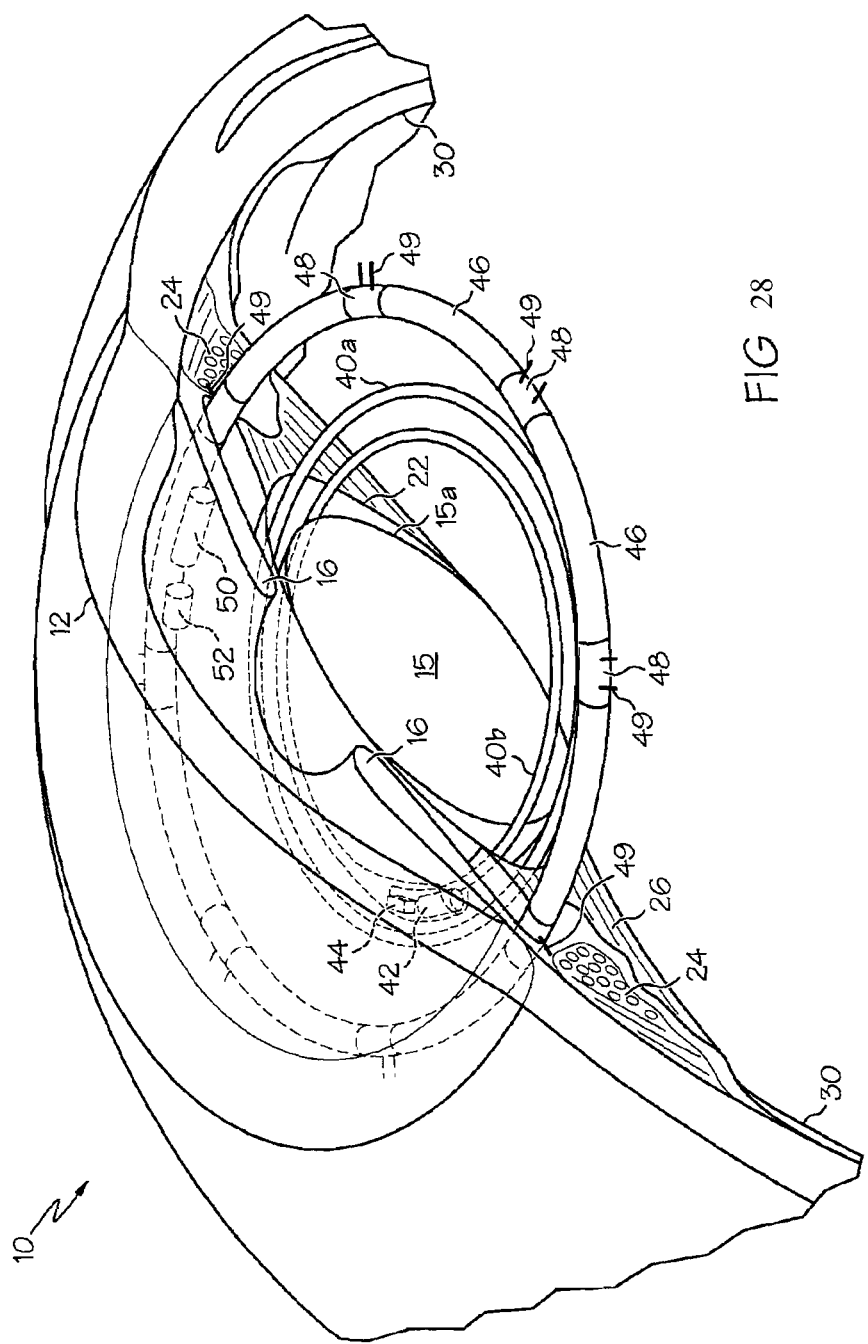
FIG. 28 is a partial cross-sectional view of the human eye showing the system of FIG. 25 after implantation into the eye as may be employed in embodiments.

In embodiments, it may be preferable to allow haptics of the IOL, with the EMG sensors embedded in them, to be in even closer proximity to the ciliary muscle surface, within the ciliary sulcus, in the same location consistent with FIG. 27. As such, the body of the synthetic electro-active (EA) intraocular lens in embodiments may be implanted within the capsular bag, and the haptics angulated or formed as to allow them to protrude outside of the edges of the capsulorrhexis and to be positioned immediately posterior to the iris root in the ciliary sulcus approximating the surface of the ciliary muscle. In embodiments, the close proximity to the ciliary muscle may allow sensitive reception of the CM action potential, CM impedance changes, CM resistive changes, and any electrical activity rendered therefrom. In addition, other filtering electrode sensors, the EA-IOL ASIC, power source, and optical components may preferably be positioned within the capsular bag, being a more favorable site for protection from ocular inflammation and internal ocular irritation, and for the optimization of optical centration.

In this or other embodiments, haptics may be positioned to emanate from the periphery of the IOL, in which embodiments total diameter would preferably be between 10 mm and 12 mm (such as 10 mm-12 mm, 10.25 mm-11.75 mm, 10.5 mm-11.5 mm, 10.75 mm-11.25 mm, or 10 mm-11 mm), including the widest diameter of the opened sensor haptics, which could be up to 14.0 mm. In this embodiment, there may be a stretching of the edges of the capsulorrhexis to allow the sensor haptics to emerge from the confines of the capsular bag for positioning in the ciliary sulcus which is external to the capsular bag. Preferably, a configuration is used such that any stretching does not result in irregular tension on the EA-IOL components confined within the capsular bag, or tilting of the optical portion resulting in degradation of optical performance.

In embodiments, an IOL may be preferably positioned within the capsular edges of a capsulorrhexis or capsulotomy. Here, the capsular opening diameter may be 4.7 mm to 6.0 mm (such as 4.7 mm-6.0 mm, 4.9 mm-5.8 mm, 5.1-5.6 mm, or 5.35 mm), depending upon optic size. Tabs on the periphery of the optical component, or a groove encircling the peripheral edge of the optic, or anterior and posterior ledges at the peripheral edge of the optic can be incorporated into the optical design. These modifications to the lens optic may allow entrapment of the IOL in the capsulorrhexis, allowing better centration. If the optic is affixed to and centered in the anterior capsular opening, the IOL design could make it preferable for the CM EMG sensors to be located on a separate ciliary sulcus ring, with wired or wireless communication to ASIC, power and IOL components within the capsular bag. In embodiments, a configuration may be used such that the capsular edge is not pulled away from the optic to such an extent that the optic entrapment and centering benefits are nullified. In embodiments, a configuration may be used such that the peripherally placed sensor haptics do not protrude from the capsulorrhexis.

In order to maintain optic entrapment in the capsulorrhexis or capsulotomy, embodiments may provide for the sensor haptics to be attached to a ring or to structures located at the optic periphery. The optic for an EA-IOL may be typically in a range between 5 mm and 8 mm (such as 5 mm-8 mm, 5.5 mm-7.5 mm, or 6 mm-7 mm). This ring or structure could be the same material as the anterior surface of the optic, and may be integrated into the anterior optical surface; or it could be a different material and contiguous to the optic. It may preferably be composed of a biocompatible, semi-flexible material such as a hydrophobic or hydrophilic acrylic. If this ring or structure is situated on the anterior axial edge of the peripheral optic, it may incorporate a groove or tabs for optical centering. The ring axial width could measure between 1 and 3 mm (such as 1 mm-3 mm, 1.25 mm-2.75 mm, 1.5 mm-2.5 mm, 1.75 mm-2.25 mm, or 2 mm), and centripetal width between 1 and 3 mm (such as 1 mm-3 mm, 1.25 mm-2.75 mm, 1.5 mm-2.5 mm, 1.75 mm-2.25 mm, or 2 mm). The ring axial width preferably is large enough for firm sensor haptic attachment and to house electronic components, yet narrow enough to afford flexibility.

A haptic ring or other haptic extension may have multiple functions, including, but not limited to functions such as the following: a) to provide an anchor for the haptic which preferably would be angulated to extend along the anterior surface of the capsular bag without distorting it, said haptic preferably fashioned in appropriate curvature and diameter of semi-flexible, biocompatible material such as hydrophobic or hydrophilic acrylic, or polymer such as a polyimide or polypropylene so as to be seated in the ciliary sulcus, said haptic preferably to function as a CM EMG action potential sensor or impedance sensor or resistance sensor and/or drivers and preferably incorporate CM sensors of biocompatible metallic material such as gold and transmitting wiring for the sensors. In embodiments haptics may preferably include other EMG filtering sensors. Haptic rings or extensions may also b) provide a housing for electronic components for the EA-IOL, such as, but not limited to, radiofrequency coil, filtering electrodes, piezo-electric components for flexible optic compression, wiring for liquid crystal, electrochemical, variable aperture or tunable accommodating lens or other electronic components; provide housing for EMG or other filtering electrodes; and c) assist in centration of the IOL within the capsulorrhexis or capsulotomy.

In embodiments, the centering modification of the IOL ring could preferably also be manufactured so that the optic would preferably be centered in a capsulotomy created in the posterior capsule. Thus, in embodiments, the multifunction haptic could preferably emanate peripheral to the optic and/or optic ring. It may preferably be attached to the biocompatible substrate of the EA-IOL, which can preferably measure 10 mm to 12 mm (such as 10 mm-12 mm, 10.25 mm-11.75 mm, 10.5 mm-11.5 mm, 10.75 mm-11.25 mm, or 10 mm-11 mm) in total diameter. The anterior capsulotomy may preferably be wider than the posterior capsulotomy, but stretching of the anterior capsule opening by the emerging haptics should preferably have little effect on optic centration or tilt, since the optic would preferably be affixed to the edges of the posterior capsule opening. The other components of the EA-IOL, including but not limited to EA substrate and housings for the power source, ASIC, RF coils, other electrode sensors, would then preferably largely be within the capsular bag.

In some embodiments, the CM sensors would receive muscle action potential (electrical) signals. In others, the CM sensors would be components of an impedance-detection sensor system. These signals would then be transferred to the Application Specific Integrated Circuit (ASIC) or other processor for further processing in conjunction with the filtering signals from interfering adjacent muscles (iris sphincter, extraocular, eyelid) and filters for radiofrequency interference so that the signal could be modulated for triggering the accommodative function of the optical portion of a synthetic intraocular lens.

The various components of an EA-IOL when fully assembled, may create a system that is larger than the typical 3-4 mm cataract incision. Although some components of the EA-IOL can be flexible, it would be preferred if the optical portion was detachable from the other components. In such an embodiment, the EA-IOL components consisting of the support plate with ASIC, battery plate, IOL driving mechanism, and support ring with attached flexible haptics could preferably be inserted separately, then the flexible optic of diameter 4-6 mm (such as 4 mm-6 mm, 4.25 mm-5.75 mm, 4.5 mm-5.5 mm, 4.75 mm-5.25 mm, or 5 mm) and thickness 0.5 to 2 mm (such as 0.5 mm-2 mm, 0.75 mm-1.75 mm, 1 mm-1.5 mm, or 1.25 mm) could preferably be subsequently inserted into the anterior chamber of an eye. The optic would then move (such as clip, snap, or slide) into position within the supportive ring or driving mechanism; and in the case of a liquid crystal or electro-chemical optic, electrical contact would preferably be achieved with pre-placed contacts; or in the case of a flexible membrane optic, the appropriate driving mechanism would preferably contact the optic.

FIG. 1 provides a table with four graphs. Two of the graphs, 110, 120, show Rhesus monkey Edinger-Westphal (EW) stimulus versus time while two of the graphs, 130, 140, show ciliary muscle (EMG) response versus time, along with accommodation as measured in diopters. These graphs show how the amplitude of a low or high brain stimulus may be measured and then interpreted as triggering a related response from the ciliary muscle. This relative relationship between the brain stimulus and the relative response or intended response of the ciliary muscle may be employed to control adjustments made to a variable optic of embodiments employing EMG sensors. These adjustments may be used in initiating, finalizing, or otherwise adjusting near focus.

For example, the EMG measurements may be similar to those observed in the Mid-Aged Rhesus monkey (equivalent to 50 yr human) experiment, which demonstrates the brain control of accommodation. Low brain stimulation (3.0 SIU) causes a low voltage EMG and mild (0.5 D) accommodation. The accommodation level is determined by an infrared phoropter. A higher amperage stimulation (7.2 SIU) causes higher voltage EMG and more accommodation (7.0 D). The E-W stimulation is in International System of Units (SIU), these are relative values of amperage displayed on oscilloscope screen; administered to an electrode placed in the midbrain at Edinger-Westphal nucleus, the center for accommodation stimulation.

It is helpful to have an understanding that the amplitude of the EMG signal is stochastic (random) in nature and can be reasonably represented by a Gaussian distribution function. In the human body, the amplitude of the signal can range from 0 to 10 mV (peak-to-peak) or 0 to 1.5 mV (rms) and the usable energy of the signal is limited to the 0 to 500 Hz frequency range, with the dominant energy being in the 50-150 Hz range. Usable signals are those with energy above the electrical noise level. In the human eye, the ciliary muscle is characterized electrophysiologically as a multi-unit smooth muscle. The voltage range varies from 20 to 150 microVolts (μV). There are two types of electrical events which occur in the non-accommodating ciliary muscle at rest: 1) the spike (100 to 150 μV) considered to originate in the motor unit, and 2) the interference pattern (30 to 100 μV) considered to be the intrinsic signal from the resting ciliary smooth muscle. In the non-accommodative state, fewer spikes of low amplitude occur (1-2 spikes/100 milliseconds) along with a lower amplitude (30-50 μV) interference pattern. As accommodation increases with increasing near focus effort, increased frequency of spikes occur (4-6 spikes/100 milliseconds) along with increased amplitude of both the spikes (100-150 μV) and interference pattern (50-100 μV). Therefore, specific algorithms may be designed to distinguish between the non-accommodative interference and spike pattern from that of the accommodative state. The resultant signal then would be used to modulate the variable focus intraocular lens. Representative algorithms may be employed that will allow variable actuation of an electro-active lens using the CM EMG signal or other signals. These algorithms may be modified according to other filters applied to EMG signals or other signals.

An exemplary algorithm to be employed by microprocessors of embodiments may be as follows:

$$S=[((A1)F1+I1)-((A2)F2+I2)]*N$$

S=output signal to electroactive lens;
N=Voltage adjustment factor;
A1=Accommodation spike amplitude;
A2=Resting spike amplitude;
F1=Accommodation spike frequency;
F2=Resting spike frequency;
I1=Accommodation spike amplitude; and
I2=Resting spike amplitude.

For example, in use, sensors and microprocessors and associated storage may carry out steps or be otherwise configured to generate an output signal to an electro-active lens using voltage measurements, frequency measurements or both. These instructions to the electro-active lens, which may be an intraocular lens, may provide focus instructions or other instructions to improve the vision of a user. These instructions may be continuous over time, be sent at periodic intervals, may be sent on an as needed basis, when requested by an electro-active lens, and at other times as well. Sensors may measure the amplitude or other feature of signal accommodation spikes (voltage or current or both) from the ciliary muscle as well as background status of signals from the ciliary muscle. Also, electrical signal frequency spikes from the ciliary muscle may also be measured along with background signal frequencies of the ciliary muscle. The spikes in amplitude and frequency may then be compared with background measurements and a difference for the frequency and the voltage calculated or otherwise determined. An adjustment factor may then be applied and an instruction sent to an IOL or other lens to focus based on the measurements and determination. This cycle of measurement and determination may be continuously repeated so as to provide real-time focusing for a user.

Figure 9:
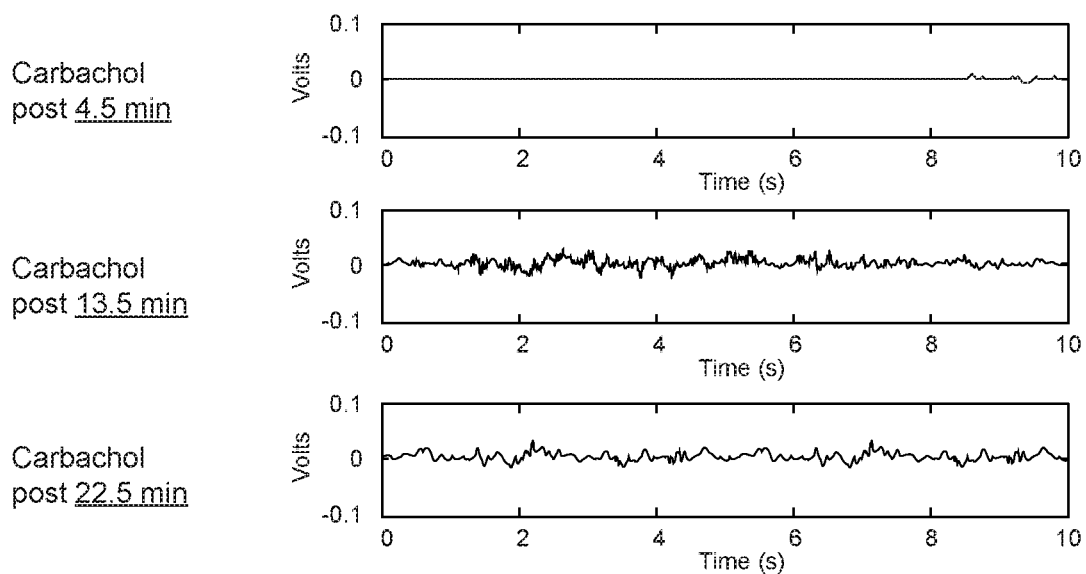
FIG. 9 shows resultant graphs of volts v. time for a carbachol experiment demonstrating Rhesus monkey ciliary muscle recordings.

FIG. 9 shows a carbachol experiment R01342. In this experiment carbachol was infused iontophoretically and recorded at 3-300 Hz. Post processing with a digital filter centered on 3.0 Hz with a bandwidth of 20 Hz was used where frequency of oscillations increased with time. Carbachol may be employed or tested to show ciliary muscle action. Carbachol placed onto the conjunctive of the eye can serve to indicate ciliary muscle action, and the CM action potential may, therefore be detected.

In embodiments, one may employ various techniques to maximize EMG recording including differential recording by appropriate electrode placement, adjusting the sensor input impedance, electronic filtering to improve the signal-to-noise ratio, bandwidth adjustment by electrode placement, and electrode geometry and placement to avoid cross-talk between adjacent muscles. A reference electrode reference (ground) is intended for providing a common reference to the differential input of the preamplifier in the electrode. In this instance, the reference electrode could be placed externally in the episcleral space and communicate with the sensor system by RF.

Figure 2:
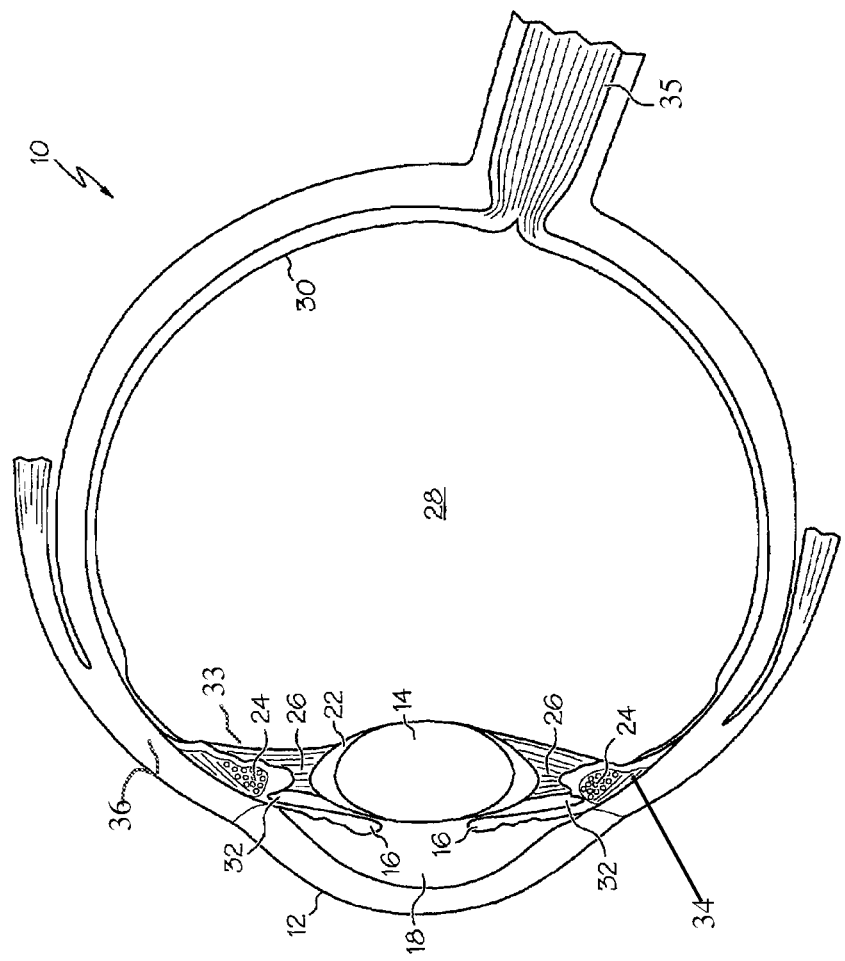
FIG. 2 is a detailed cut-away view of a human eye.

FIG. 2 illustrates a human eye 10 whose vision may be corrected in accord with embodiments. Devices and systems may be implanted in and around the eye 10 and processes may be applied to the eye 10 in accord with various embodiments. Labeled in FIG. 2 are the anterior chamber 18 between the cornea 12 and iris 16, a posterior chamber behind the iris containing a bi-convex natural crystalline lens 14, a vitreous chamber 28 behind the lens 14 containing vitreous humor, and a retina 30 at the rear of the vitreous chamber 28. In operation, light is focused by the eye 10 by being refracted through the cornea 12 and then refracted again through the lens 14 and upon the retina 30 for transmission to the brain by the optic nerve 34. The lens 14 is encased in a native lens capsule or capsular bag 22, which is attached about its equator or periphery to the ciliary muscle 24 by zonular fibers 26, called zonules of Zinn. Between the iris 16 and the ciliary muscle 24 is an annular crevice-like space called the ciliary sulcus 32. Internal to the ciliary muscle 24 is the internal globe cavity, the intravitreal space 33, and between the ciliary muscle and sclera 36 is the choroid and suprachoroidal space 34.

While the cornea 12 provides a significant portion of the refractive power of the eye, the capacity for accommodation is primarily contributed by the lens 14, because of its inherent elastic properties. The inner ends of the zonules 26 are attached to the lens capsule 22, and the outer ends are attached to the ciliary muscle 24. The ciliary muscle 24 is part of a sphincter-like ciliary body, which opens when it is relaxed, thereby generating tension on the zonular fibers 26. The ciliary muscle 24 is relaxed in the unaccommodated eye, and the ciliary body therefore assumes its largest inner diameter, which in turn causes a tension on the zonules 26. In this state, the zonules 26 are caused to pull radially outward on the lens capsule 22, flattening and making the lens 14 less convex. Thus, when the ciliary muscle 24 is relaxed, the refractive power of the lens is relatively low and the eye is focused for clear vision of distant objects. The lens capsule 22 is comprised of membrane-like, elastic, optically clear anterior and posterior walls or capsules. When the ciliary muscle 24 contracts it moves forward and inward, thereby relaxing the outward pull of the zonules 26 on the equator of the lens capsule 22 and reducing the zonular tension on the lens 14. The lens 14 becomes more rounded, so that the eye is focused for clear vision of nearby objects. Therefore, for near vision, the ciliary muscle contracts and releases tension on the zonular fibers 26, allowing the lens 14 to elastically rebound and thicken, and, in a manner of speaking, "relax" back to its more convex and spherical natural state. Modern cataract surgery typically involves removing the cloudy contents of the eye's natural lens 14 while leaving the clear outer membrane or capsule 22 (also referred to as a capsular bag) to hold a new, artificial intra-ocular lens (IOL) in place. The sensors in embodiments may be positioned in various locations in and around the eye 10. These include in the intra capsular bag, the ciliary sulcus, the subconjunctival, suprachoroidal space, intrascleral, and even outside the eye 10 on a contact lens positioned on the cornea 12.

Figure 3:
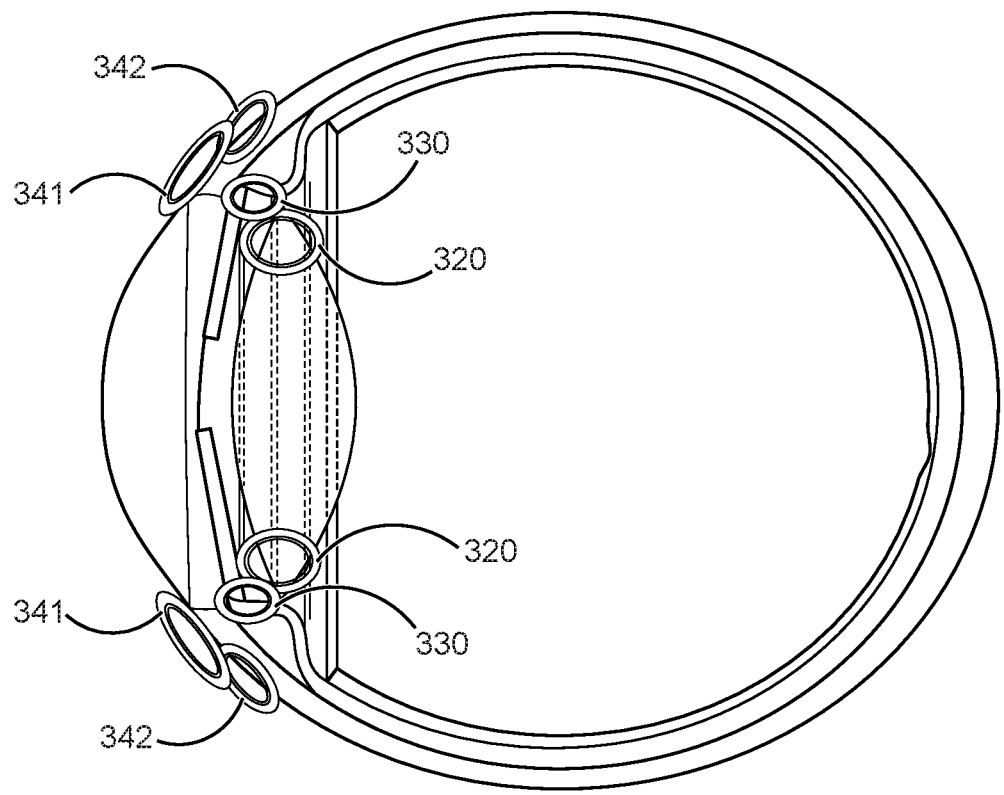
FIG. 3 is a schematic side-view of the human eye with exemplary locations of electromyography sensors as may be employed in embodiments.

FIG. 3 shows various sensor positions as may be employed in embodiments. The actual modifiers of vision may be positioned within the eye, such as an intra-ocular lens and outside the eye on spectacles or a contact lens or a corneal inlay. In embodiments, one or more EMG sensors may preferably be positioned in proximity to the muscle. However, the electrodes may be configured consistent with this disclosure to perform their function and preferably filter out unwanted signals from neighboring muscles. Any of the vision modifiers could be monocular or binocular. Locations for the EMG ciliary muscle sensor may include the intra capsular bag 320, the sulcus 330, the subconjunctival, and even outside the eye, on a contact lens, 341-342.

Also, depending upon the desired electronic lens or device to be activated, the EMG sensors can be placed in a variety of locations. A first choice for intra-capsular sensor location may be a posterior chamber (in-the-bag) intraocular lens. Increased muscle tone from frequent accommodation would enhance a microinvasive glaucoma surgery (MIGS) device through increased aqueous outflow, no matter which sensor location is used.

In embodiments, a ciliary sulcus sensor may preferably be chosen to activate a capsular bag IOL, but for patients who have a first generation single-focus IOL, especially if already wearing spectacles due to refractive error, would benefit from a secondarily implanted sensor system that would activate an electronic spectacle lens. This may help to reduce or eliminate the bifocal, which can be a danger to elderly patients going up and down stairs.

In embodiments, a subconjunctival sensor may be used to activate any of the external lenses or a corneal inlay (and even a phakic IOL for myopia). Later on, such a sensor may also be beneficial if the patient develops a cataract, the same sensor could wirelessly activate a secondarily implanted electronic IOL (now, sans internal EMG sensor); or in the rare event of a sulcus or intra-capsular sensor failure, the subconjunctival sensor could be implanted to continue the accommodative function. Still further, in embodiments, the contact lens sensor may preferably activate the contact lens Presbyopia-Correcting (PC) device. It may also activate a PC-IOL, inserted without EMG sensor, or in the rare event of a failed internal EMG sensor.

Figure 4:
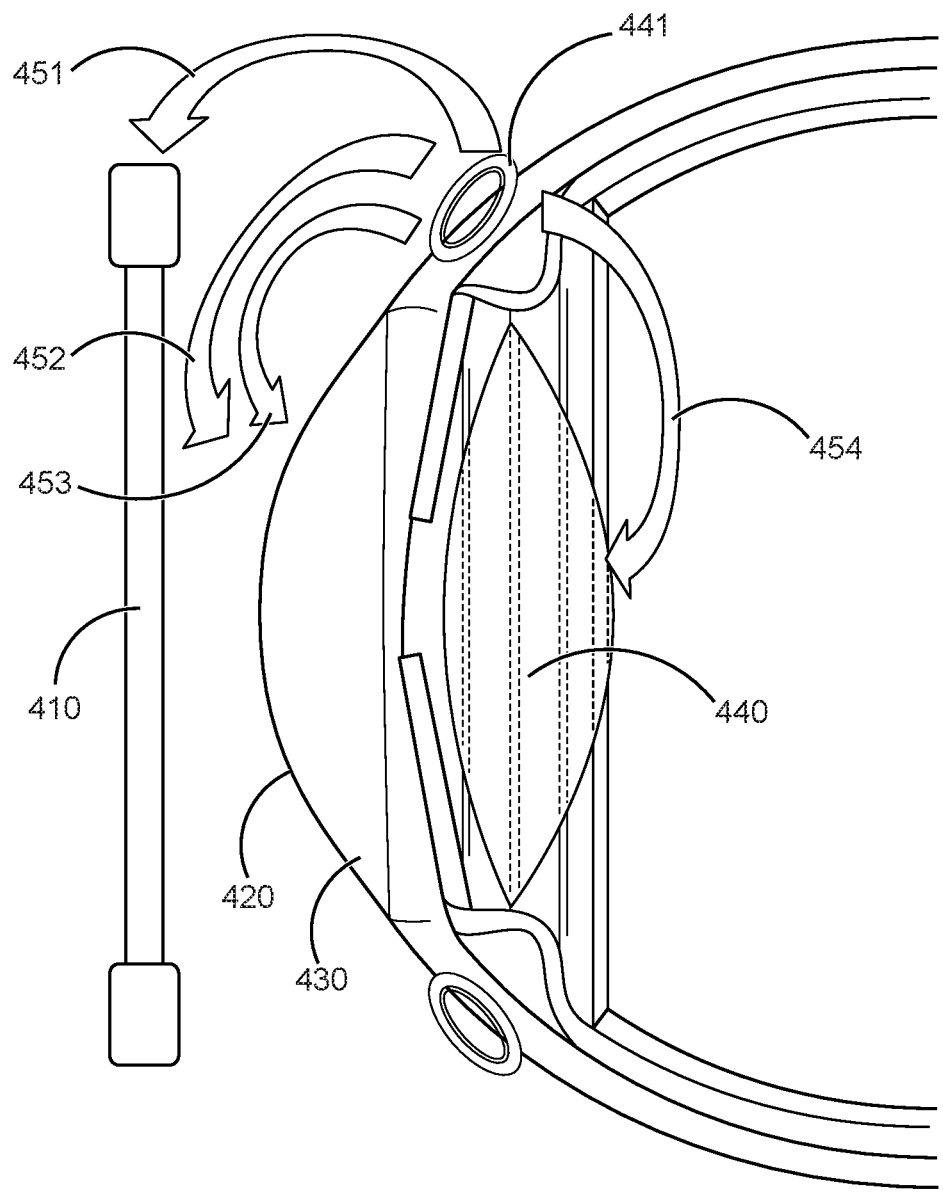
FIG. 4 is a schematic partial side-view of the human eye with EMG sensors and possible locations of electro-active accommodation devices as may be employed in embodiments.

FIG. 4 shows various vision correction devices. These include spectacle lenses 410, contact lenses 420, corneal inlays 430, and intraocular lenses 440. These correction devices may be active in embodiments and may be configured to repeated cycle and focus depending upon sensed signals exemplifying muscle action potential as well as nerve action potential or other triggering detected signal.

Figure 5:
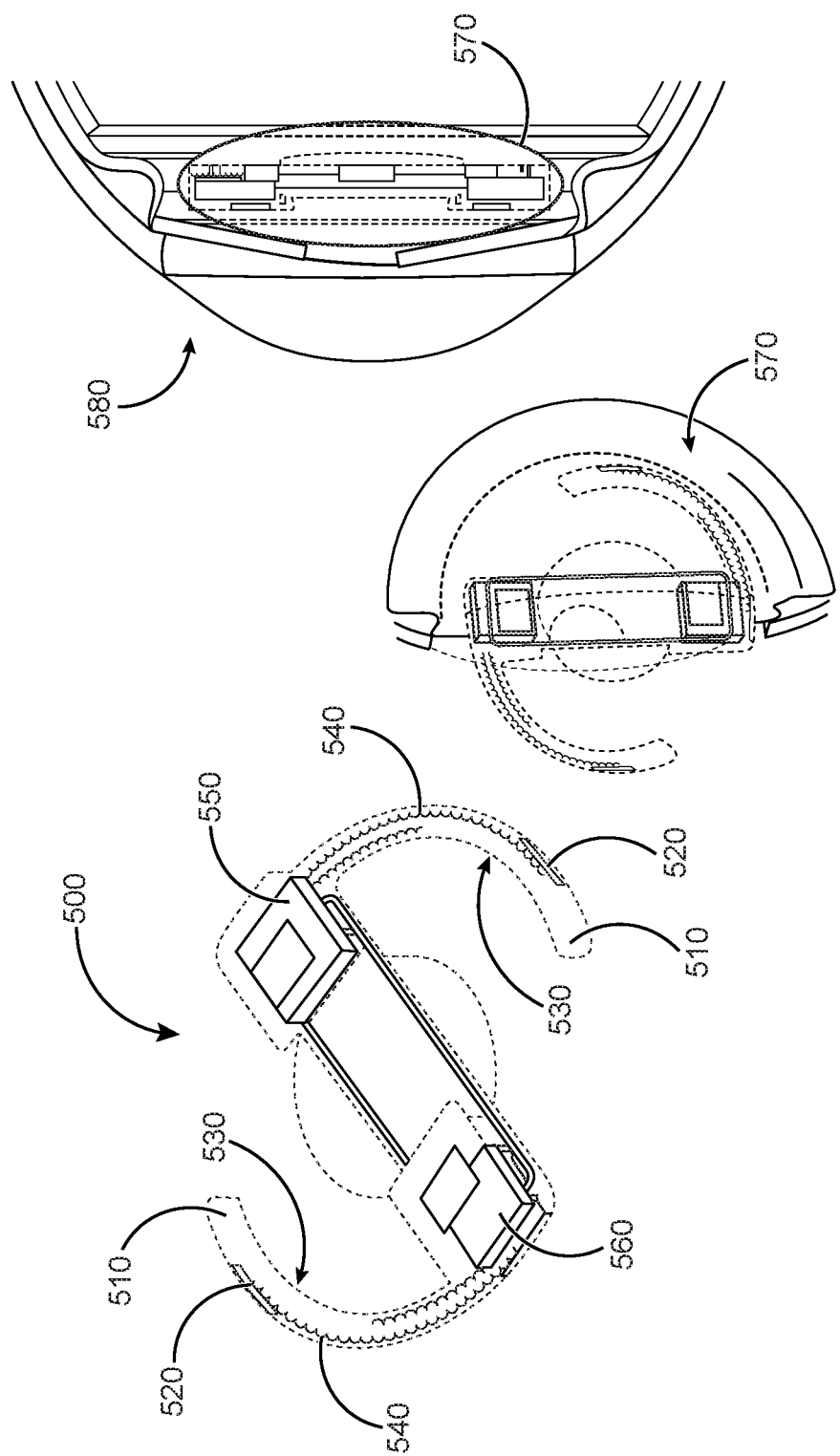
FIG. 5 shows an electro-active intraocular lens with haptic intracapsular bag sensors and exemplary positioning as may be employed in embodiments.

FIG. 5 shows an intracapsular bag sensor 500 as may be employed in embodiments. These sensors may be included with an electro-active accommodating IOL and have multiple sensors 520 on foldable haptics 530 and casing 510 for filtering. These sensors may further include RF coils 540 around the haptics, inductive batteries 550 and Application Specific Integrated Circuits 560 (ASIC). The sensor 500 may be foldable and may be inserted in the eye 580 of a patient through a corneal incision, where the haptics can serve to stretch the capsular bag 570 to preferably come into close proximity to the ciliary sulcus. The haptics may also be shaped to provide centering forces for any IOL when the IOL with haptics is positioned at the eye of a user.

Figure 6:
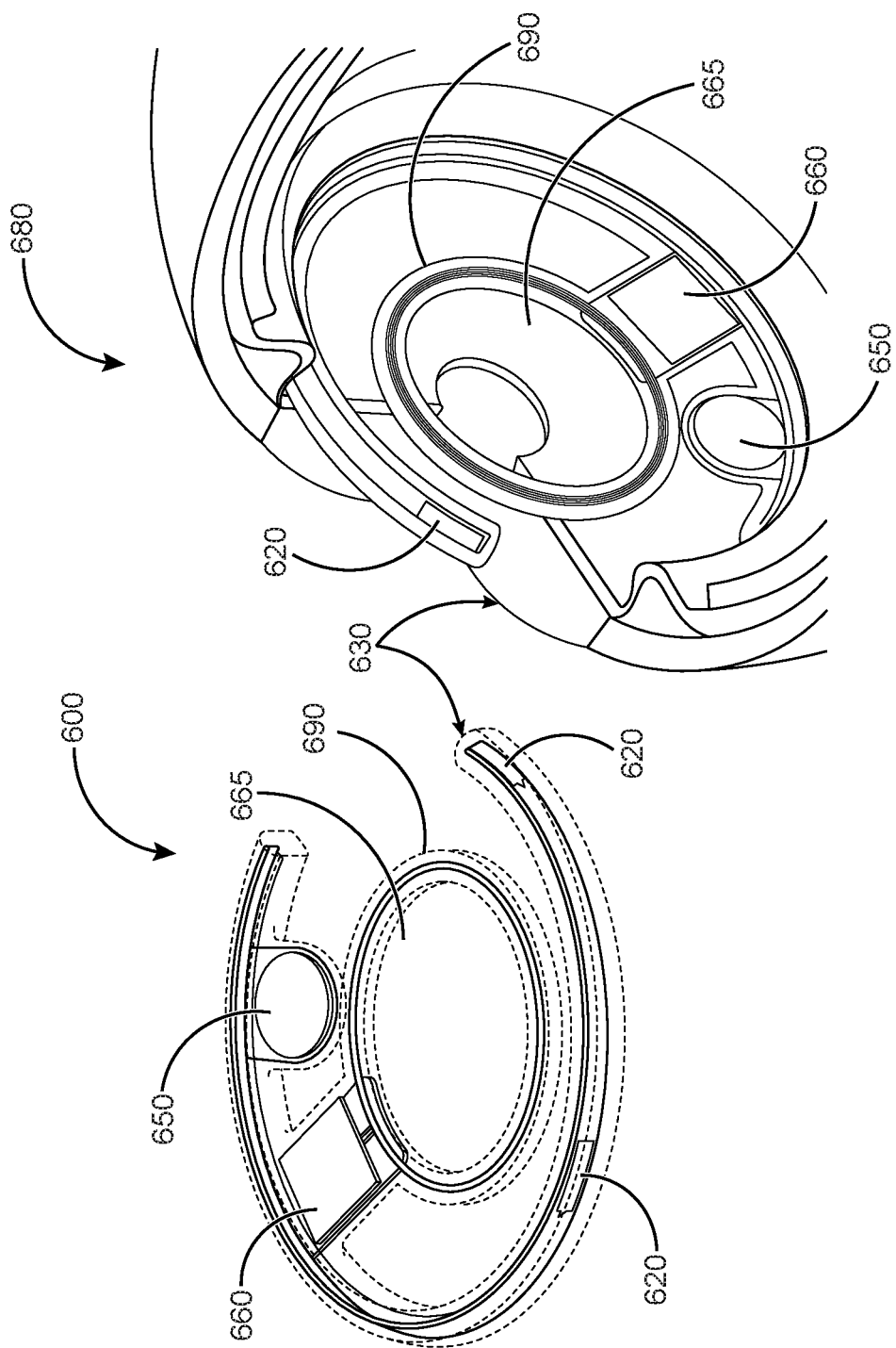
FIG. 6 shows a sulcus ring sensor and exemplary positioning as may be employed in embodiments.

FIG. 6 demonstrates how a ciliary sulcus EMG Sensor 600, may be inserted through a 3 mm incision in the eye 680.

The EMG sensors of embodiments may be configured for receiving the electrical activity of the ciliary muscle, a plurality of sensors embedded within the positioning haptics of an electro-active accommodating IOL, which system may include power source, electronic circuitry, Application Specific Integrated Circuit (ASIC), radiofrequency or wireless communication component 660, and a variable focus optical component 665. A battery 650 is also labeled. In embodiments some of the sensors may target the action potential of the ciliary muscle, and others target the iris sphincter muscle for filtering. In certain embodiments, a plurality of sensors 620 function in pairs of driving and sensing sensors to measure the impedance of the ciliary muscle of an eye. In embodiments, haptics 630 may have a diameter of 10.0 to 14.0 mm and a curvature and compressive force to assure close approximation to the ciliary muscle within the ciliary sulcus. In embodiments, haptics 630 may emanate from a supportive ring or structure 690 adjacent to the optic 665, so that the haptics 630 are positioned anterior to the anterior capsule and extend peripherally to lie within the ciliary sulcus adjacent to the ciliary muscle.

Also, in embodiments, the optic 665 may include a ridge or projections to facilitate entrapment within an anterior capsulotomy or capsulorhexis of an eye. In embodiments, electronic components of an EA-IOL may be positioned within the capsular bag and the electronic components are detachable from the optical component and can be assembled surgically within an eye. Still further, in embodiments, the electronic components may be detachable from the support components, and can be assembled surgically within an eye. Likewise, in embodiments, electronic components may be detachable from the haptic component, and can be assembled surgically within an eye.

In embodiments, components may communicate by direct connection, contact or wire. Components may communicate by wireless radiofrequency. Sensors employed in the haptics, such as those shown in FIG. 6, may include one or more of: a glucose monitor, a pressure monitor, a biochemistry monitor, or an electrophysiology monitor.

Figure 7:
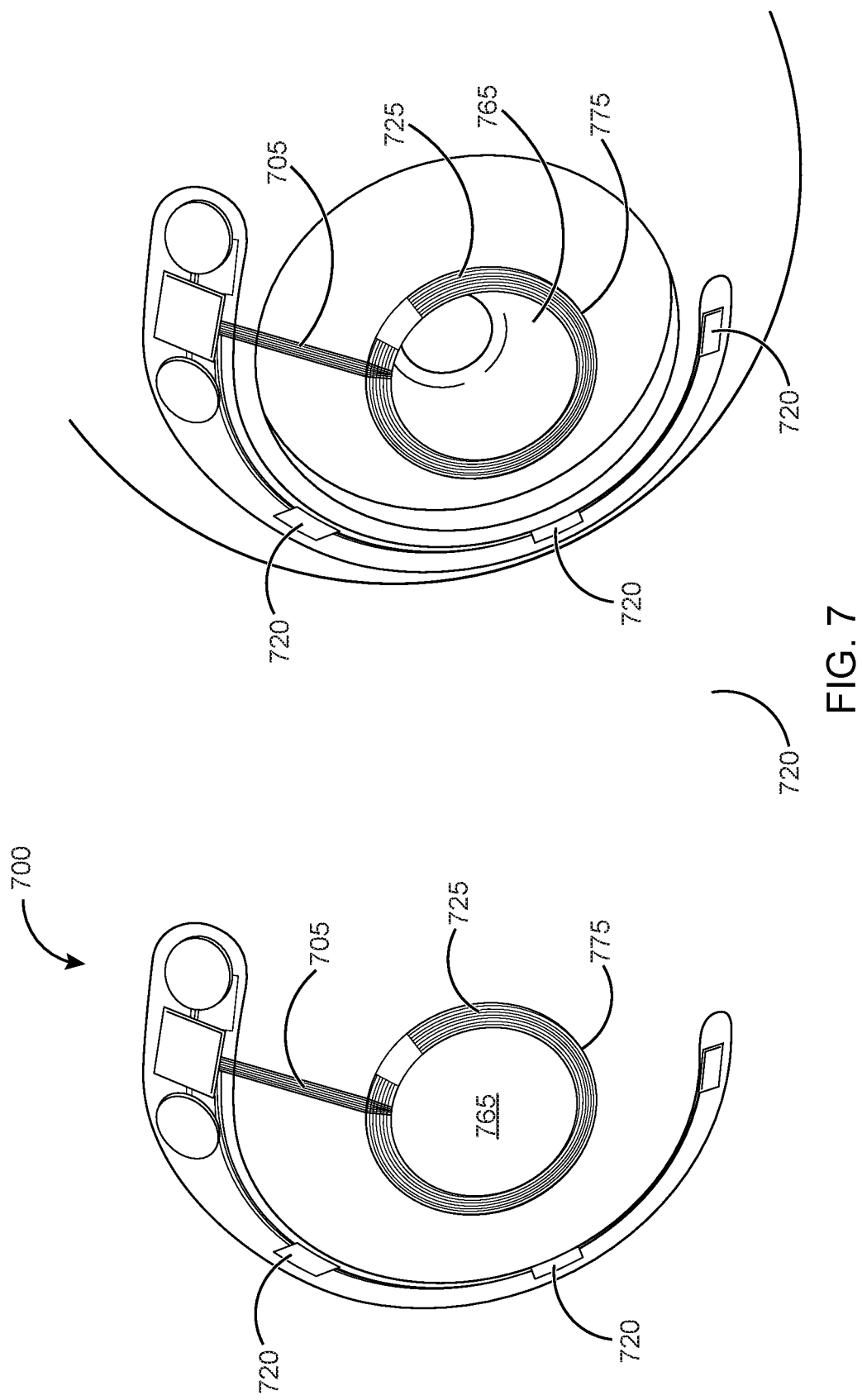
FIG. 7 shows an accommodating corneal inlay and subconjunctival sensor as well as exemplary positioning as may be employed in embodiments.

FIG. 7 shows Presbyopia-Correcting (PC)-Corneal inlay 700. As can be seen, a thin wired corneal connection 705 to the subconjunctival sensors 720 is provided but this connection may be wireless as well. As with the sulcus ring in FIG. 6, the subconjunctival EMG Sensors of FIG. 7 may be inserted through a superficial, 3 mm incision. Also labeled in FIG. 7 is a coil 725, an accommodating lens 765, and a reference electrode 775.

Figure 8:
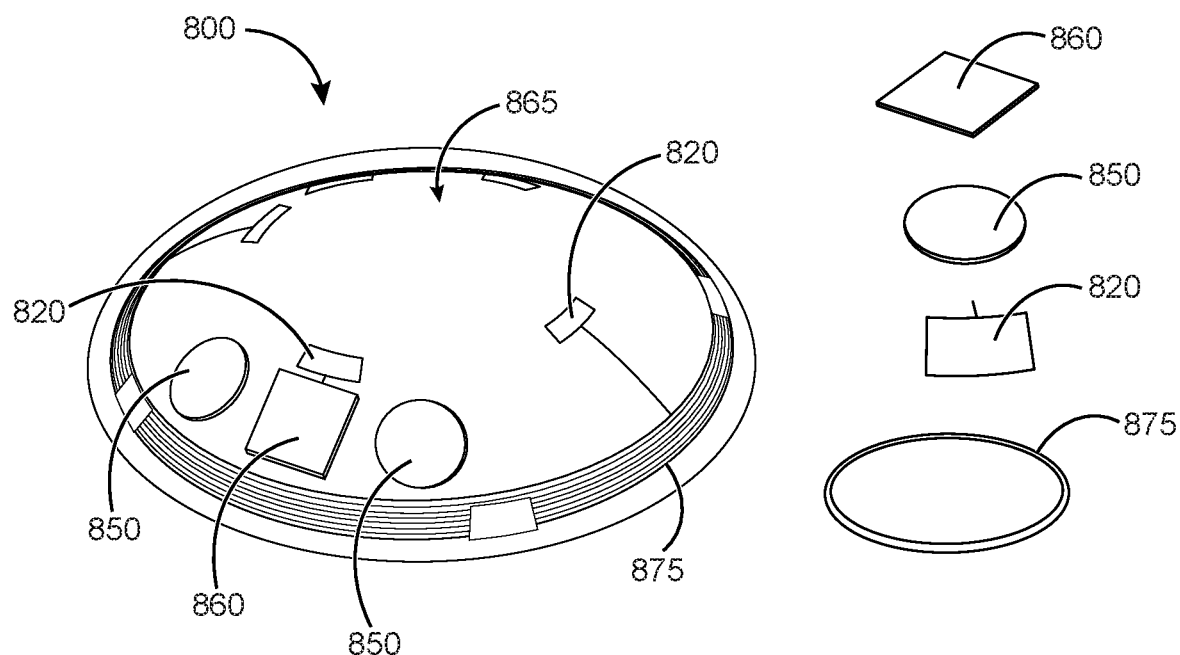
FIG. 8 shows a contact lens sensor and accommodating contact lens as may be employed in embodiments.

FIG. 8 shows a contact lens EMG sensor, with a multiplicity of sensors 820 and componentry. PC-Contact Lens 800 with a liquid crystal, electrochemical or variable aperture optic 865 are shown. Thus, embodiments also include applications where components, including sensors, may be positioned outside of the eye. Also labeled are an ASIC 860, batteries 850, and a coil 875.

In embodiments, EMG sensors could be positioned on a ciliary sulcus ring (CSR) which can be implanted in the ciliary sulcus via intra-ocular endosurgery (now commonly performed in procedures such as endocyclophotocoagulation which incorporates a fiber-optic device) to ensure accurate placement in the sulcus. The ciliary sulcus ring or other placement can communicate either through radiofrequency (RF) wireless transmission with the other components placed upon an IOL within the capsular bag, or alternatively, an exterior contact lens or other exterior devices. The CSR supports at least one and typically a series of CM signal sensors. Each EMG receiver can include contacts or miniaturized electrodes in the form of CM probes, typically in pairs, for entering the CM or for application adjacent to or in close proximity to (1-5 mm) the CM. The EMG receivers could be conductive flat or conductive biocompatible metallic plates, such as gold, or a conductive metal covered by a biocompatible thin substance such as a polymer.

CM sensors can be flat or tubular areas contiguous with the main body of the CSR or other support, and can provide electrical, mechanical or chemical recognition of a CM signal via miniaturized electrode probes or contacts. Embodiments can employ sensors such as electromyographic probes that can detect a muscle signal by electrical/neuroelectrical means, or by chemical/neurochemical means, and also through mechanical movement of the CM, or a combination of these means. EMG electrodes or probes that may be repurposed and modified for use as an internal sensor supported on the CSR include those disclosed in U.S. Pat. No. 7,941,201 to Chiou et al., disclosing a microprobe array structure which detects a neuroelectrical signal through skin.

The CSR may be made of polymethylmethacrylate (PMMA), with or without a collamer coating, or a combination of biocompatible metals having conductive plates. The plates can serve as the sensors/EMG contacts, and may include fine wire appendages as probes for entering the CM. The composition of the probes could be a metallic material or an alloy both biocompatible and conductive.

In embodiments, the CM signal sensors may not be positioned within the ciliary sulcus. Since a muscle action potential can be detected through layers of dermal tissue, in a like fashion the sensors could be placed within the capsular bag, or within the subconjunctival or episcleral space on the surface of the eye, or within a contact lens that lies on the surface of the eye in proximity (1-8 mm) from the ciliary muscle. The sensors could consist of a thin metallic plate or wire attached to the ASIC either wired or wirelessly by RF. If the sensor is located within the capsular bag, the close proximity (1-3 mm) and aqueous environment would allow rapid transmissibility of the neuroelectrical signal or AP.

In embodiments, the CM signal sensors can be in the form of a first sensor positioned within the ciliary sulcus, such as a CSR, and a companion sensor positioned on one of the IOL components located within the capsular bag. Movement of the first sensor relative to the companion sensor provides the ability to detect CM movement in response to the accommodative reflex, however small. Further, a series of CM sensors can be supported on both the CS ring and the in-the-bag components and the degree of movement of these sensors relative to one another can provide a very sensitive means for detecting an accommodative signal from the CM.

In embodiments, paired sensors the first sensor on the ciliary sulcus or the ciliary/zonular complex and the second imbedded in the subconjunctival space superficial to the sclera could communicate relative motion. In embodiments sensors may be a conductive metal such as gold or titanium, or a piezoelectric material with biocompatible covering, one of which has an electrical connection wired or wirelessly to the ASIC, battery, and EA IOL. During voluntary accommodation, whether induced naturally or by external stimulation, the movement of the CM would change the relative distance of the sensors, such that a signal is captured and sent to the ASIC triggering the accommodative EA IOL or other accommodative device, such as contact lens or spectacles.

In preferred embodiments, EMG sensors have the ability to filter unwanted signals from nearby muscles such as the iris sphincter muscles, the extraocular muscles (EOMs) (especially the medial rectus which has the dual function of accommodative convergence and abduction for right and left gaze) and the eyelids. Positioning the sensors in a circular pattern can allow the ASIC to be programmed to filter the EOMs. Also, the summation effect of a circular pattern and opposing or differential electrodes can reinforce the AP of the CM. If the CSR is fashioned as an incomplete circle, the open space may be positioned relative to the horizontal rectus muscles so an additive effect of the medial rectus and CM could be used to trigger the accommodative stimulus. However, the iris sphincter muscle also responds in a circumferential fashion to both accommodative and light stimulus, whereas the CM only to accommodation. The iris AP would preferably be shielded from the CM sensor by directional orientation of the sensors posteriorly toward the CM in certain embodiments. In addition, the sensors can be constructed with an electrical barrier of non-conductive material on the anterior or iris-side aspect of the sensors in certain preferred embodiments.

In embodiments, the iris constriction response, as measured by electrodes oriented towards the iris, could be added to the CM response. Thus the summated response of the CM and iris could signal an accommodative device through the ASIC, but not the iris response alone, thereby eliminating the iris light response as an accommodative stimulus.

The eyelid muscles also create an AP. Since these muscles are a much greater distance from the sensors when located as a CSR or in the capsular bag, the sensitivity of the sensors may preferably be modulated in embodiments such that the eyelid AP is not detected. In addition, the ASIC may be programmed in embodiments to respond to the unique characteristics of the CM AP, which again, respond in a circumferential manner as compared to the superior/inferior or vertically oriented blink reflex.

A problem with passive electrodes originates from trying to combine low-noise analog circuitry and fast logic in the front end. Interference from the digital circuitry when it is coupled to the sensitive analog input circuitry occurs. Embodiments may, therefore, perform analog signal processing at the electrode. An active transducer may form a signal source with a low output impedance which can serve to eliminate the need for shielded wires. The application of active electrodes of course requires a small electrical current that may be supplied by a battery system.

In embodiments, EMG electrodes or sensors may serve to capture the action potential of the CM and these electrodes or other sensors may be placed in a position other than the ciliary sulcus. The sensor could be embedded in a rigid gas-permeable (RGP) or soft contact lens (SCL). This thin-wire electrode of conductive metallic material such as gold or platinum could be embedded in any one of commonly used polymers, for example in polymethylmethacrylate (RGP), or hydrogel, or silicone SCL. Thus, these sensors may be used for capturing the electrical activity generated by the CM in its action of accommodation. In embodiments, and as is shown in FIG. 8 for example, two or more sensors may be located in the periphery of a large diameter 12-20 mm SCL so as to be situated in proximity to the CM, overlying it. In addition, other EMG sensors may be positioned more centrally to capture the AP of the iris sphincter muscle, so as to use the iris AP concurrently with the CM AP in algorithms appropriate to driving an EA IOL. The CM sensors and the iris sensors could be positioned circumferentially in the SCL so that input can be used in the algorithm in order to provide summation or filter unwanted electrical activity of other ocular and eyelid muscles, such as those muscles that drive accommodative convergence, gaze movements, and blink. The output of the EMG sensor could be used to power an EA CL or spectacles.

In embodiments, electrodes or other sensors that can be used to capture the AP, impedance change, and resistance change of the CM, possible locations previously referenced are the ciliary sulcus and contact lens. In addition, it may be desirable to place electrode sensors in other locations to maximize the ability to receive the electrical activity of the CM. One or more electrodes could be implanted into the subconjunctival, tenon, or episcleral space immediately adjacent to the CM. This would allow accurate electrical transmission from the CM and also permit simple surgical insertion. The electrode would communicate via wireless transmission to other electronic components of a targeted device, such as an accommodative IOL, accommodative CL, or accommodative spectacles.

Furthermore, embodiments may also implant the sensors even closer to the CM via a conjunctival incision and scleral incision, to position a biocompatible sensor electrode adjacent to the CM intrasclerally, or suprachoroidal, or intravitreal and in direct contact with the CM.

Embodiments for detecting the action potential signal, impedance change, and resistance change of the ciliary muscle of the human eye may include placing one or more electrodes near or on the ciliary muscle, processing a signal sensed by the one or more electrodes and in certain embodiments using additional electrodes within the same, or both eyes to remove unwanted or conflicting signals or noise. This sensed and perhaps corrected signal may be electronically transmitting to a processor or controller that drives one or more variable focus lenses. Various permutations and supplementations may also be used in embodiments, and these permutations and supplementations may comprise electrode(s) receiving the ciliary muscle action potential, and other ocular muscle action potentials, where the potentials were either naturally produced or artificially induced by external electrical stimulation. Moreover, these electrodes may comprise metallic rings, and/or metal strips, and may be manufactured from a biocompatible metal or a metallic substance encased in a biocompatible material. In embodiments, electrode(s) may be active in which they would form a signal source with low output impedance to enhance external noise filtering. The transmission from electrodes may be through a direct connection between said electrodes and a processor or controller as well as being wirelessly transmitted a short distance. This short distance may be 8 mm or less, 3 mm or less and 1 mm or less. Other distances may also be considered. The electrode(s) may be located internally or external to the ciliary muscle or targeted ocular muscles, whether suprachoroidal, episcleral, intrascleral, or subconjunctival as well as within a contact lens or other positioning component.

Various electromyographic sensor configurations may also be employed. These may include various systems and discrete devices, components, and subcomponents. Embodiments may be configured to provide variable focus and may be designed to provide near vision correction for the human eye and may include instances where the variable focus may be activated by a sensor that detects the action potential of the ciliary muscle as it attempts to induce an accommodative response in the human eye. This near vision correction may include changing the focus of a variable focus lens. Such embodiments may include variable focus lens that may be activated by a sensor detecting the action potential whether naturally produced or artificially induced by external electrical stimulation; variable focus lens comprises liquid crystal electroactive lens; a variable aperture lens, a compressible lens whose power is adjusted by piezoelectric plates; a lens configured and sized to be inserted into the human eye; a lens configured and sized to be worn as a contact lens on the surface of the cornea; and a lens configured and sized to replace the normal crystalline lens of the human eye.

Processes may include detecting action potential signal, impedance change, or resistance change of the ciliary muscle of the human eye by placing one or more electrical sensors near or on the ciliary muscle, and one or more in close proximity such that relative motion of the sensors is detected due to muscle contraction. A signal or signals may be transmitted to a processor or controller that drives one or more variable focus lenses. In embodiments, sensors may detect the ciliary muscle action potential or other change, and its movement, whether naturally produced or artificially induced by external electrical stimulation. Thus, in embodiments, electro-active ciliary muscle sensors can serve to detect the action potential or electrical activity generated within a muscle.

Figure 10:
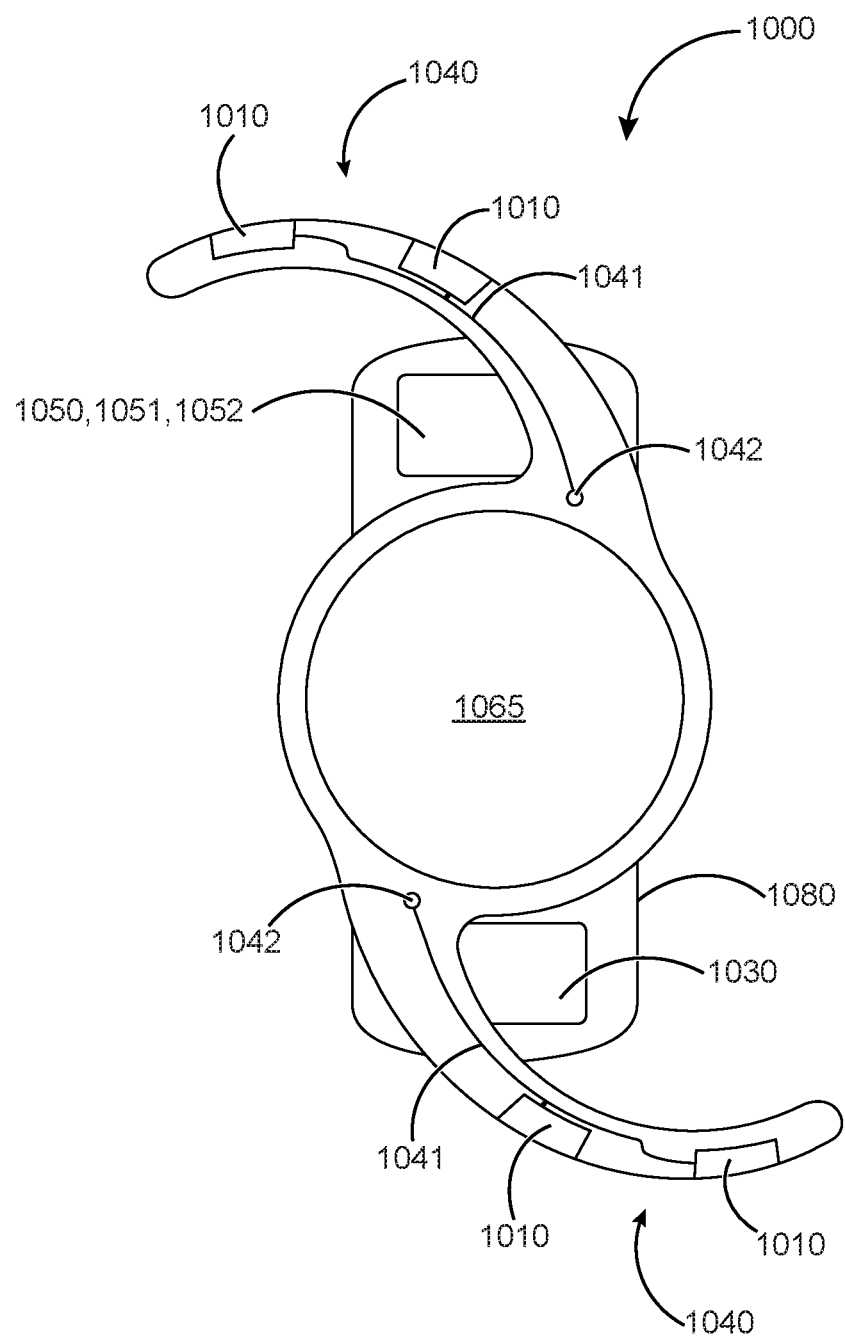
FIG. 10 shows an electroactive intraocular lens with flexible haptic sensors and sensing electrodes as may be employed in embodiments.

FIG. 10 shows an electroactive intraocular lens with flexible haptic sensors and sensing electrodes as may be employed in embodiments. Sensing electrodes 1010, support ring 1020, filtering electrodes 1030, flexible haptic 1040, battery 1051, bottom inductance loop 1080, optic 1060, ASIC 1050, connectors 1042, and driving mechanism 1052 are labelled in FIG. 10. This top down view shows how the flexible haptics 1040 swirl outwardly from the central optic 1065 and can serve to apply centering force for the EA-IOL 1000. The flexible nature of the haptic arms 1040 and the position of the sensing electrodes 1010 on the flexible haptic arms 1040 allow the sensing electrodes 1010 to be positioned near the ciliary muscle when the EA-IOL 1000 is implanted at the eye of a user. In this EA-IOL two flexible haptic arms 1040 are shown, however, in other embodiments, there may be more and their shape and position may be different. In preferred embodiments flexible haptic sensors will be paired such that they can apply opposing forces when implanted. The transmission lines 1041 serve to connect the electrodes 1010 with the other components and terminate at the support ring 1020.

Figure 11:
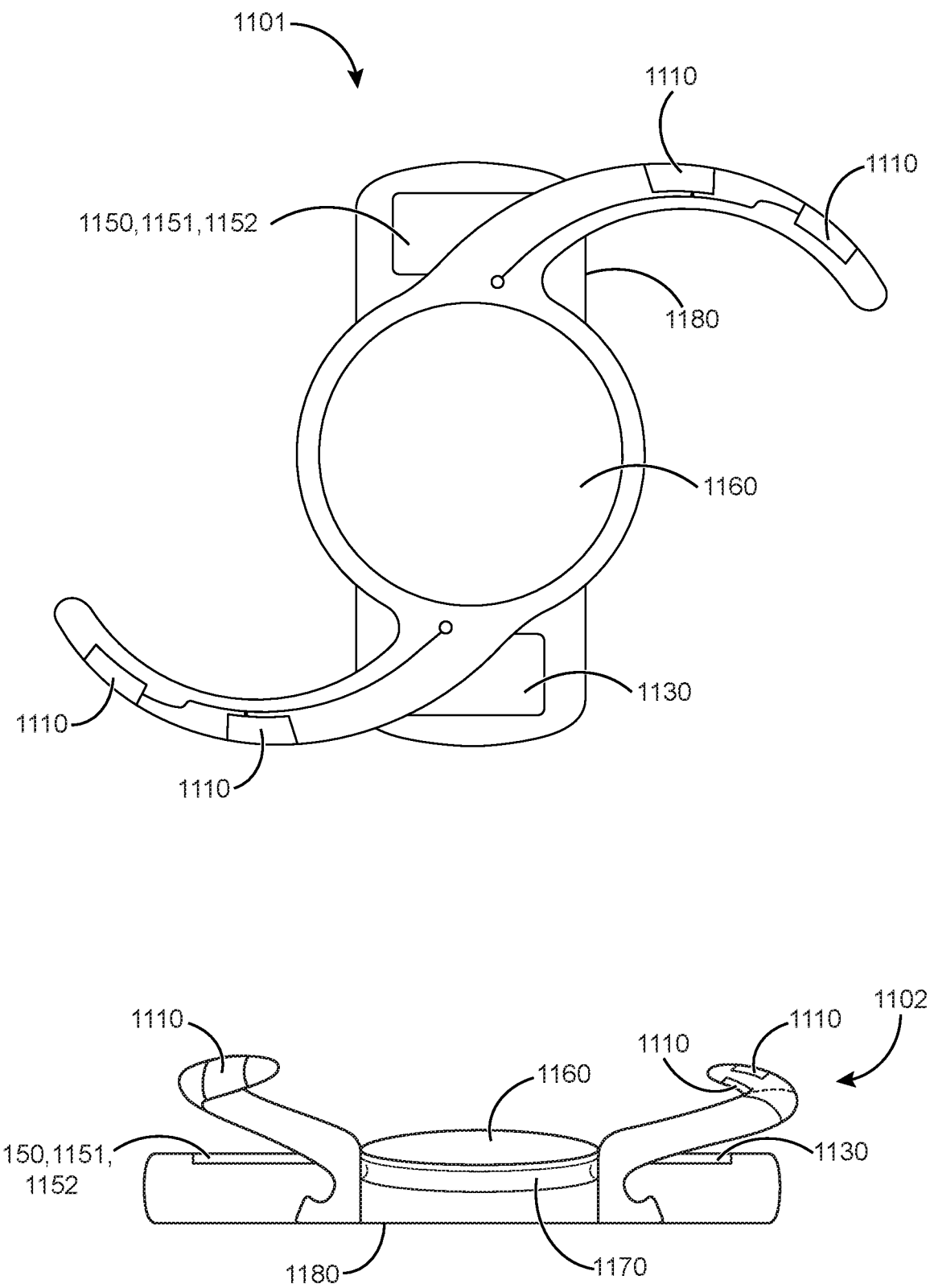
FIG. 11 shows top and side views of electroactive intraocular lenses with flexible haptic sensors and sensing electrode sensors as may be employed in embodiments.

FIG. 11 shows top 1101 and side 1102 views of electroactive intraocular lenses with flexible haptic sensors and sensing electrodes sensors as may be employed in embodiments. A seating groove 1170 can be seen in the side view below the optic 1160. Also labeled are the sensors 1110, the haptic arms 1140, the filtering elements 1130, the battery 1151, the ACIS 1150, and the driving mechanism 1152. As can be seen from the side view the haptic arms may curl up and away and may serve to position the sensors 1110 at different planes. As can also be seen in FIG. 11 the bottom plate 1180 may be somewhat rectangular in shape and may serve to contain the battery, ASIC, driving mechanism, and filtering electrodes.

Figure 12:
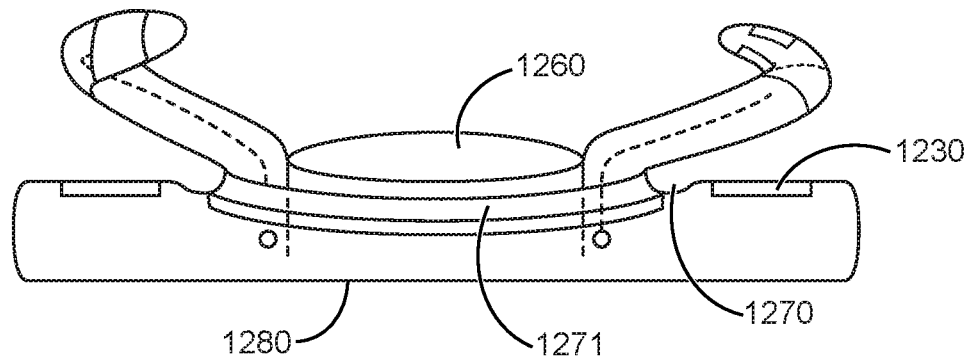
FIG. 12 shows side views of electroactive intraocular lenses with flexible haptic sensors and sensing electrode haptic sensors having various grooves and other features as may be employed in embodiments.
Figure 12:
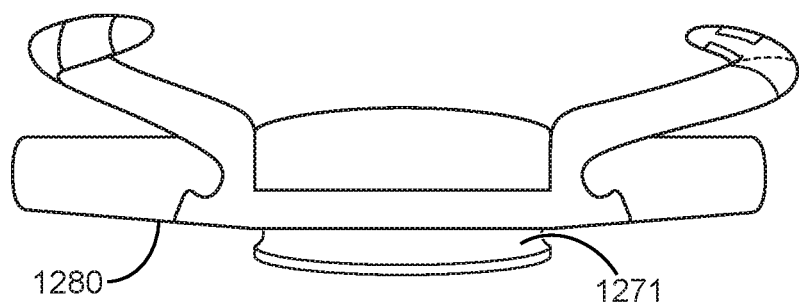

FIG. 12 shows side views of electroactive intraocular lenses with flexible haptic sensors and sensing electrodes haptic sensors having various grooves and other features as may be employed in embodiments. FIG. 12 shows a filtering sensor 1230 located below a haptic arm and sensor. This filtering sensor may be used to sense background signals used to cancel out noise and hone in on true CM signals or other signals to be used for vision correction. The indentation for groove 1270 and the groove 1271 are labelled, as is the optic 1260. These side views of an EA-IOL also show that the bottom loop 1280 may have different configurations and may be grooved or otherwise configured to promote installation and seating of the EA-IOL.

Figure 13:
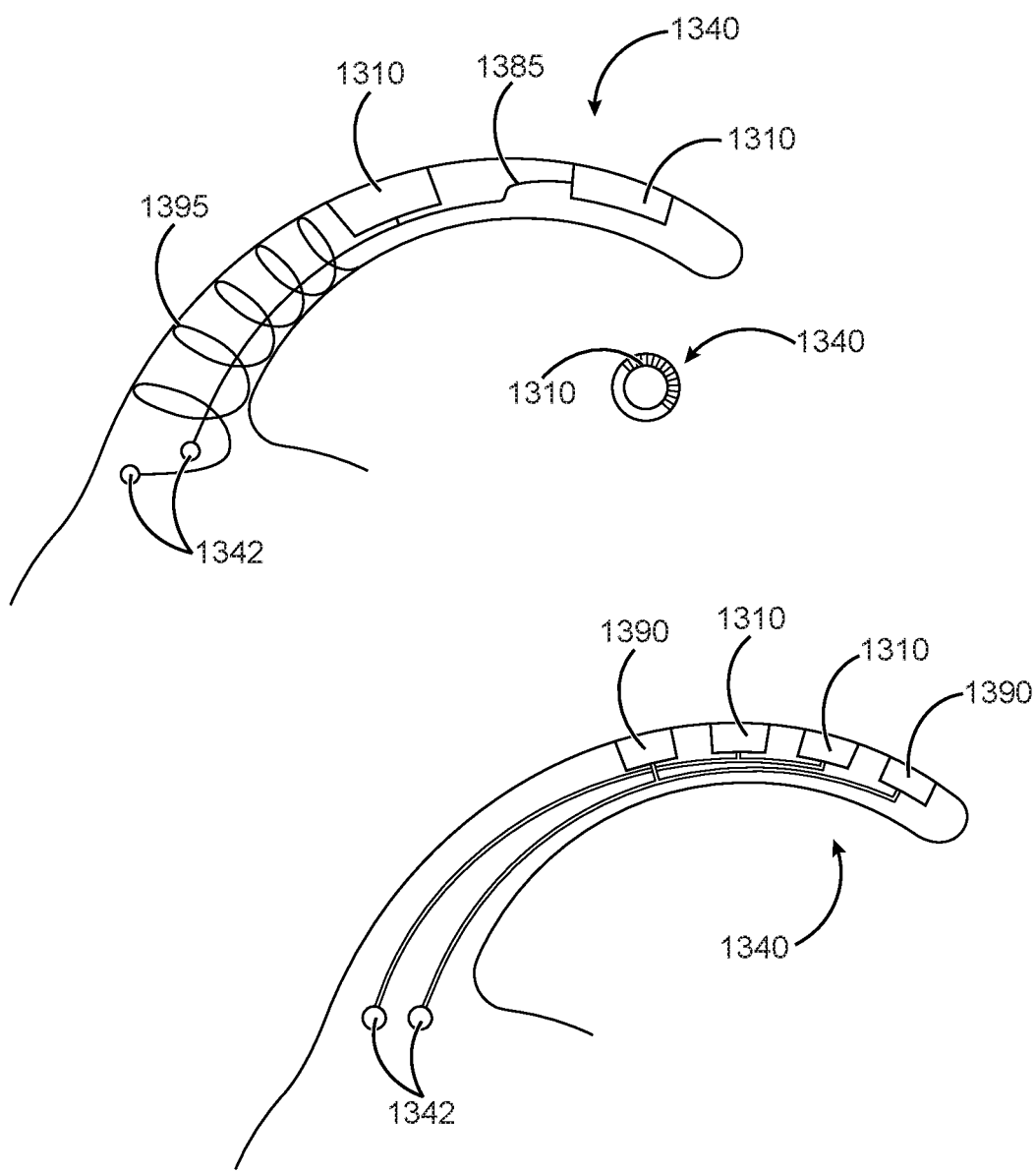
FIG. 13 shows enlarged schematic views of haptic sensors with sensing and/or driving electrodes as may be employed with embodiments.

FIG. 13 shows enlarged schematic views of haptic sensors with sensing electrodes as may be employed with embodiments. The haptic EMG sensor is shown above the haptic impendence sensor in FIG. 13. In the haptic EMG sensor electrode sensors 1310 are positioned near the tip of the haptic arm 1340 and are connected via wires 1385 to connectors 1342. These connectors 1342 allow information to be sent from the sensors 1310 to other components of the haptic EMG sensor or related systems. The cross-sectional view 1350 shows that the electrode sensors 1310 may occupy a significant portion of the wall of the haptic arm. The cross section also shows that the haptic arm may have a circular cross-section. Radio Frequency (RF) coil 1395 is also positioned within the haptic arm and may be used to receive signals from the implant site and transmit the signals to components of the haptic or other system components via the connectors 1342.

The haptic impedance sensor is shown in the lower half of FIG. 13 and includes both sensing electrodes 1310 and driving electrodes 1390. Each of these electrodes may be connected to connectors 1342 and may be used for impedance sensing as described herein. As can be seen, the RF coil is not shown to be present in the haptic arm for the impedance sensor and the driving electrodes need not be present in the haptic arm 1340 for the EMG sensor.

Figure 14:
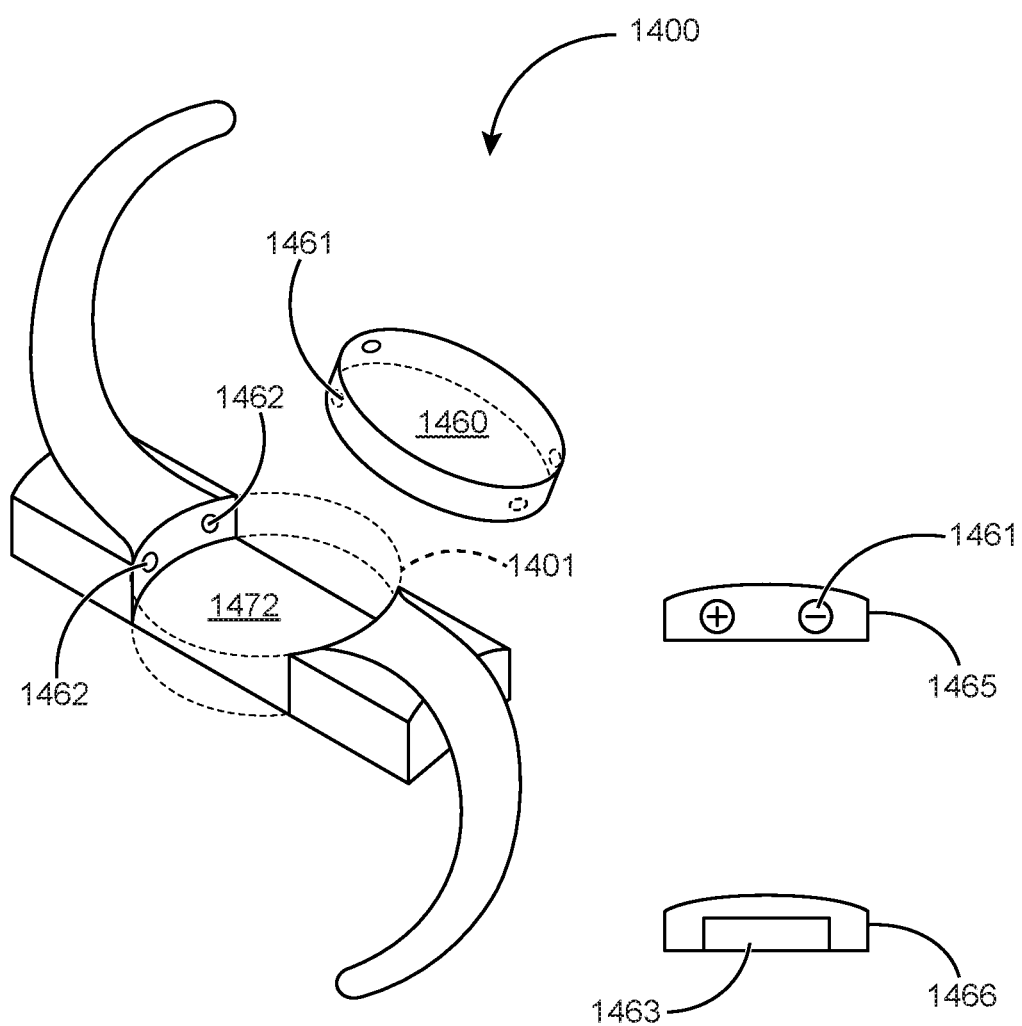
FIG. 14 shows an electroactive intraocular lens with detachable optic as may be employed in embodiments.

FIG. 14 shows an electroactive intraocular lens with various detachable optics as may be employed in embodiments. The flexible ring 1401 may serve to hold the detachable optic 1460 in place in the EA-IOL 1400, and contacts 1461 on the optic 1460 may be positioned to touch contacts 1462 on the receptacle. The optic end view 1465 shows contacts 1461 and how they can meet the contacts in the receptacle. Optic end view 1466 shows how the contact 1463 may be an electrically activated magnetic, or preferably a piezoelectric (PZO) plate configuration. A corresponding PZO plate 1463 may be present in the receptacle 1472. Thus, the optic may be coupled and decoupled from the EA-IOL 1400 and may have various contact points and types for power communications, and activation among and between the optic and the other components of the EA-IOL 1400.

Figure 15:
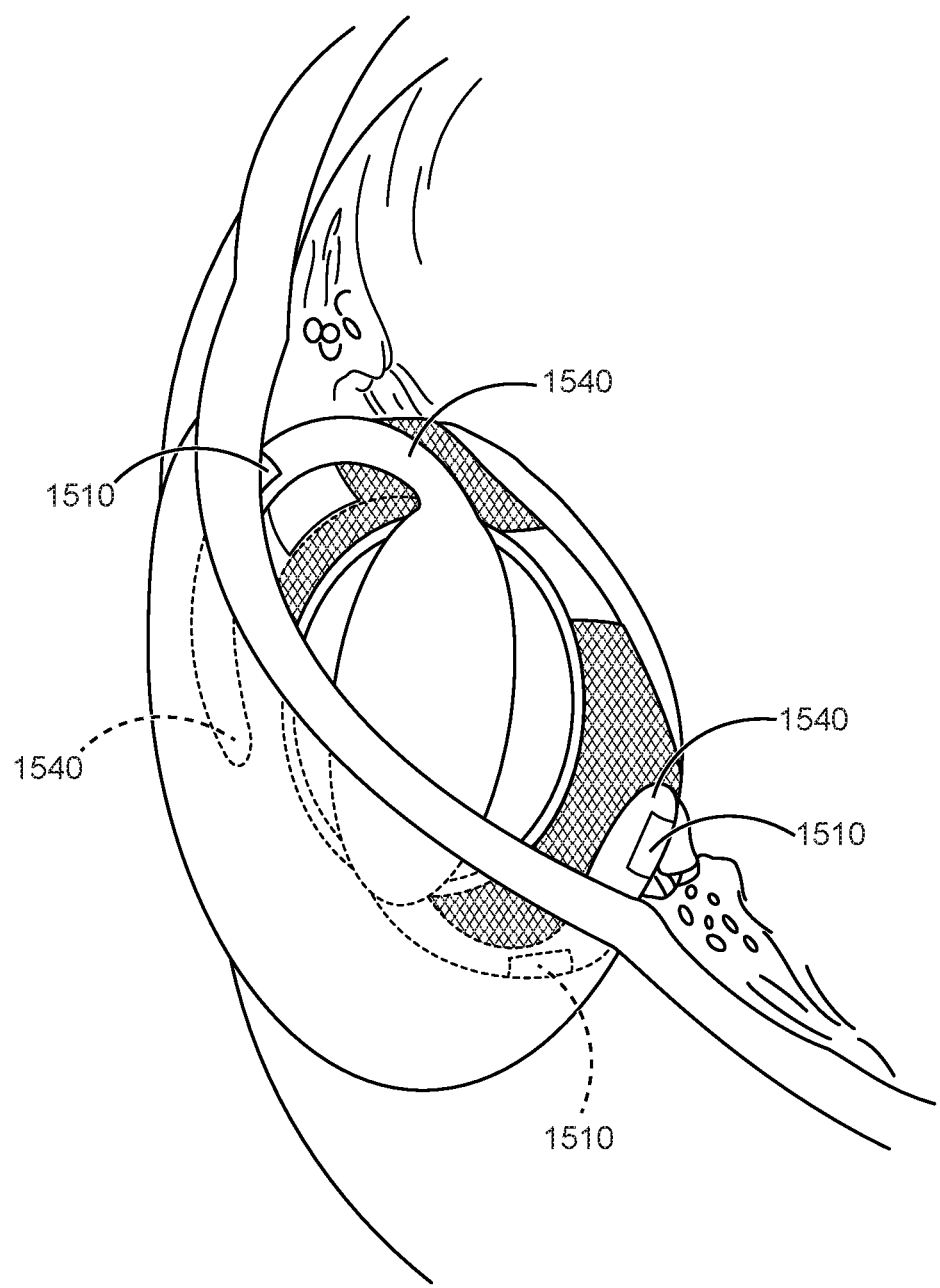
FIG. 15 shows a partial sectional view of an electroactive intraocular lens with flexible haptic sensor and sensing electrodes positioned at the eye of a user as may be employed in embodiments.

FIG. 15 shows a partial sectional view of an electroactive intraocular lens with flexible haptic sensor and sensing electrodes positioned at the eye of a user as may be employed in embodiments. As can be seen in this view, the haptic arms 1540 extend outwardly and serve to center the EA-IOL and also position sensors 1510 in the haptic arms near target signal generators like the ciliary muscle.

Figure 16:
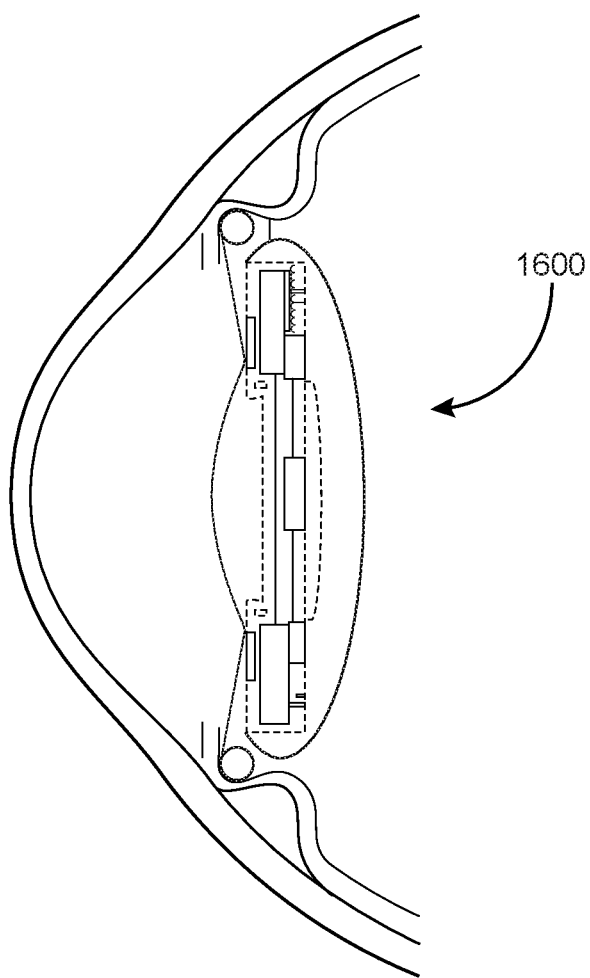
FIG. 16 shows a side view of an electroactive intraocular lens with grooves for anterior capsule positioned at the eye of a user as may be employed in embodiments.

FIG. 16 shows a side view of an electroactive intraocular lens 1600 with grooves for anterior capsule positioned at the eye of a user as may be employed in embodiments. As can be seen, the EA-IOL 1600 is centrally seated in capsule bag and the grooves are suited for the anterior capsule and employs features and components of other embodiments described herein.

Figure 17:
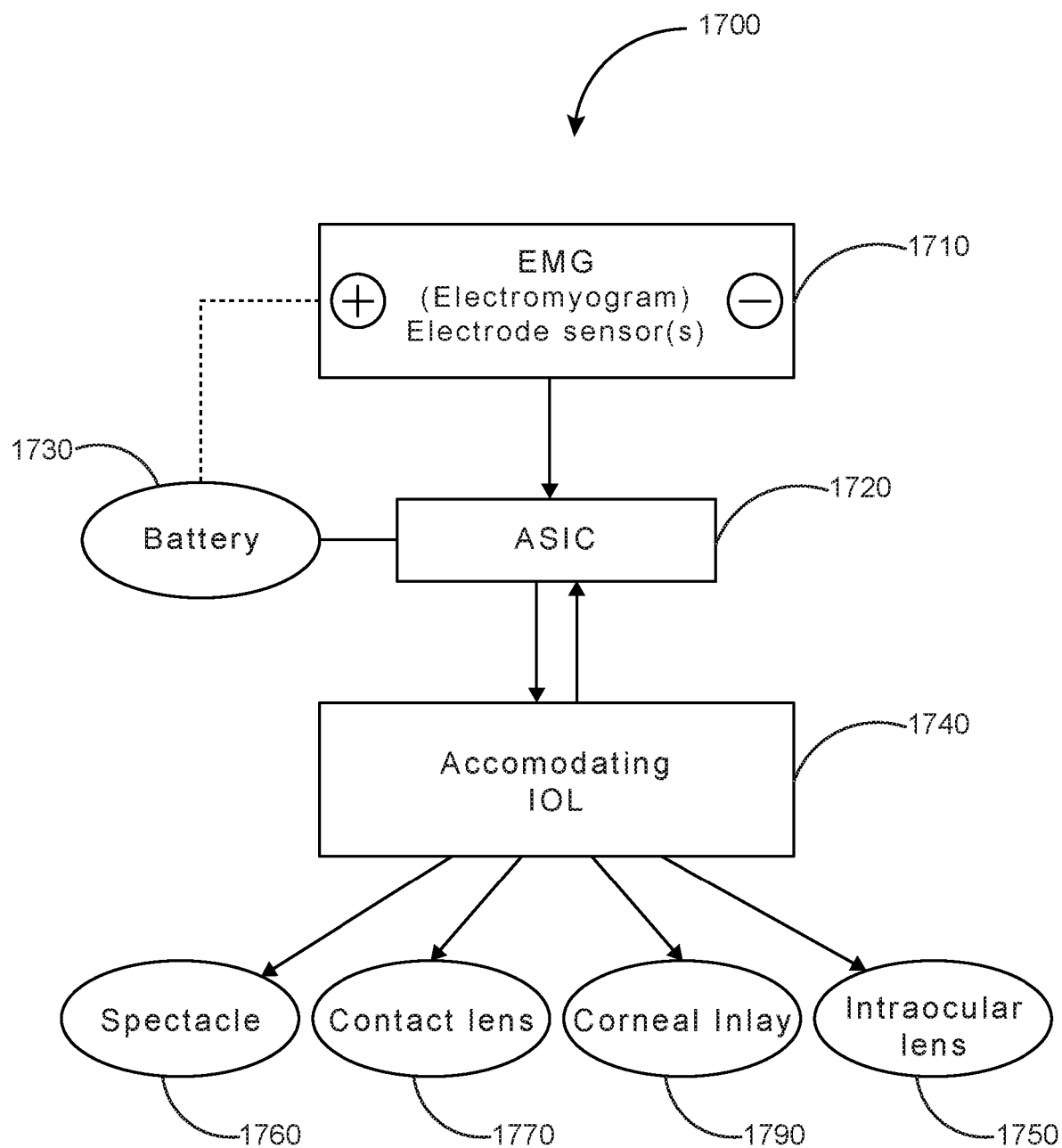
FIG. 17 is a schematic of an intraocular lens system as may be employed in embodiments.

FIG. 17 shows a schematic of a corrective system 1700 as may be employed in embodiments. Various sensors 1710 with radio frequency or wired communication paths to an ASIC 1720 may be used with power provided by a battery 1730 or other power source and vision being corrected by a variable focus lens. This signal can then be processed in an ASIC 1720, which signal can be used to drive an accommodating electroactive lens 1740; the system 1700 may use an inductively charged battery such as Li-MH; the A-EA lens such as corneal inlay 1790, or pseudophakic posterior chamber lens 1750 within or around the capsular bag, anterior to the native crystalline lens such as in an electro-active phakic lens, or sent externally by wireless signal to an external lens such as accommodative spectacle 1760 or contact lens 1770.

In certain embodiments, as may be used to efficiently detect the CM signal, the sensor should preferably be as close as possible to the CM muscle, where the ciliary sulcus can serve as a preferred location because of proximity to the muscle and ease of access through a conventional cataract incision.

Furthermore, in order to acquire the action potential, impedance change or resistance change of a specific muscle or group of muscle motor units, it is preferable to have two conducting electrodes proximate to the target muscle, an anode and a cathode. Preferably, these electrodes may be close to the belly of the muscle in order to obtain the purest signal. In reference to the ciliary muscle, which extends in a circular fashion inside the eye, specific arrangements may be provided so as to maximize the sensitivity of the sensor electrodes.

Certain design parameters can serve to increase the strength of the signal. For example, sensor locations imbedded onto a circular ring or haptic implanted within the ciliary sulcus. The sensor material could be a biocompatible, conductive metallic material such as gold or gold film, foil or a gold etched surface. It may be desirable, in order to increase the signal acquisition ability of the sensing device, to have continuity of the sensing material around the circumference of the substrate material, which can preferably consist of a biocompatible, flexible material such as acrylic, collamer, or silicone. It would be useful to have a core of Nitinol wire, or other biocompatible substrate to which the electrode would be annealed.

Figure 18:
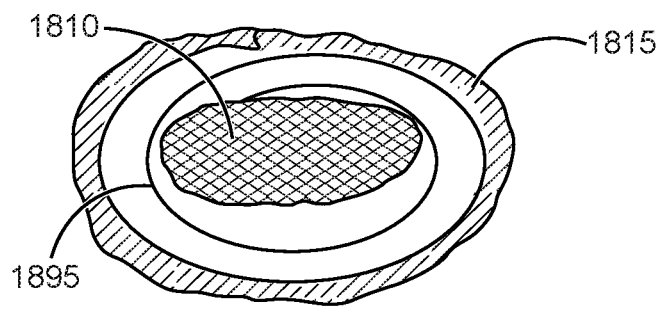
FIG. 18 shows perspective views of an electrode sensor and radio frequency coil as may be employed in embodiments.
Figure 18:
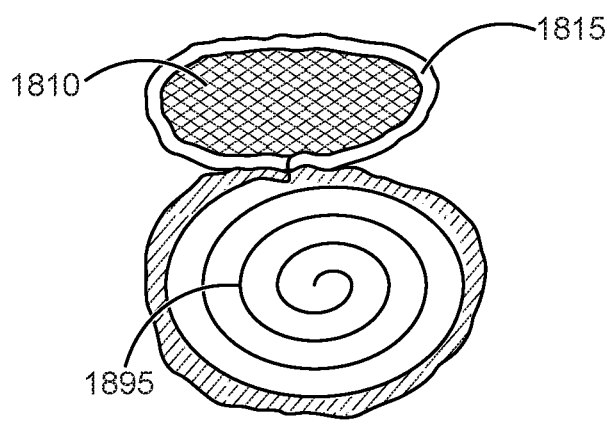
Figure 18:
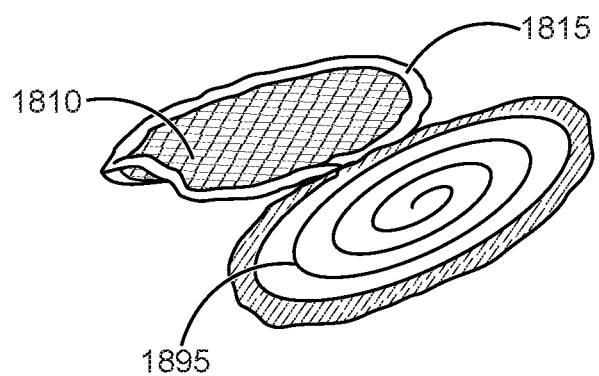

FIG. 18 shows sensors with electrode plates and radio frequency coils 1895 as may be employed in embodiments. These sensors 1810 may comprise silicone or hydrogel substrate 1815 or both in embodiments. The sensor electrodes would preferably be composed of a biocompatible, conducting metal such as gold, and embedded within a flexible substrate such as a biocompatible silicone or hydrogel. The electrodes may communicate with the sensor system, including an ASIC; and a battery may be included in the system for powering one or more of the sensors, ASIC and variable focus accommodating IOL. Any of the electrode sensors could communicate by wireless (such as a radiofrequency coil) attached to the sensor electrode, or direct wire.

Other locations, although not as desirable due to distance from the CM, shielding by other tissues, or difficulty in access for surgical implantation, are also plausible. These other viable locations (and their potential difficulties) include: the ocular surface via contact lens electrode (distance, episcleral and scleral shielding, artifacts from eye movement, irritation of the patient's conjunctiva); episcleral (distance, scleral shielding, requirement for separate incision); scleral or intrascleral (surgical difficulty and possible bleeding); suprachoroidal (surgical difficulty and possible bleeding); and infrachoroidal/intraocular(surgical access technically difficult, possibility of vitreous base traction with subsequent retinal tear or detachment).

Figure 19:
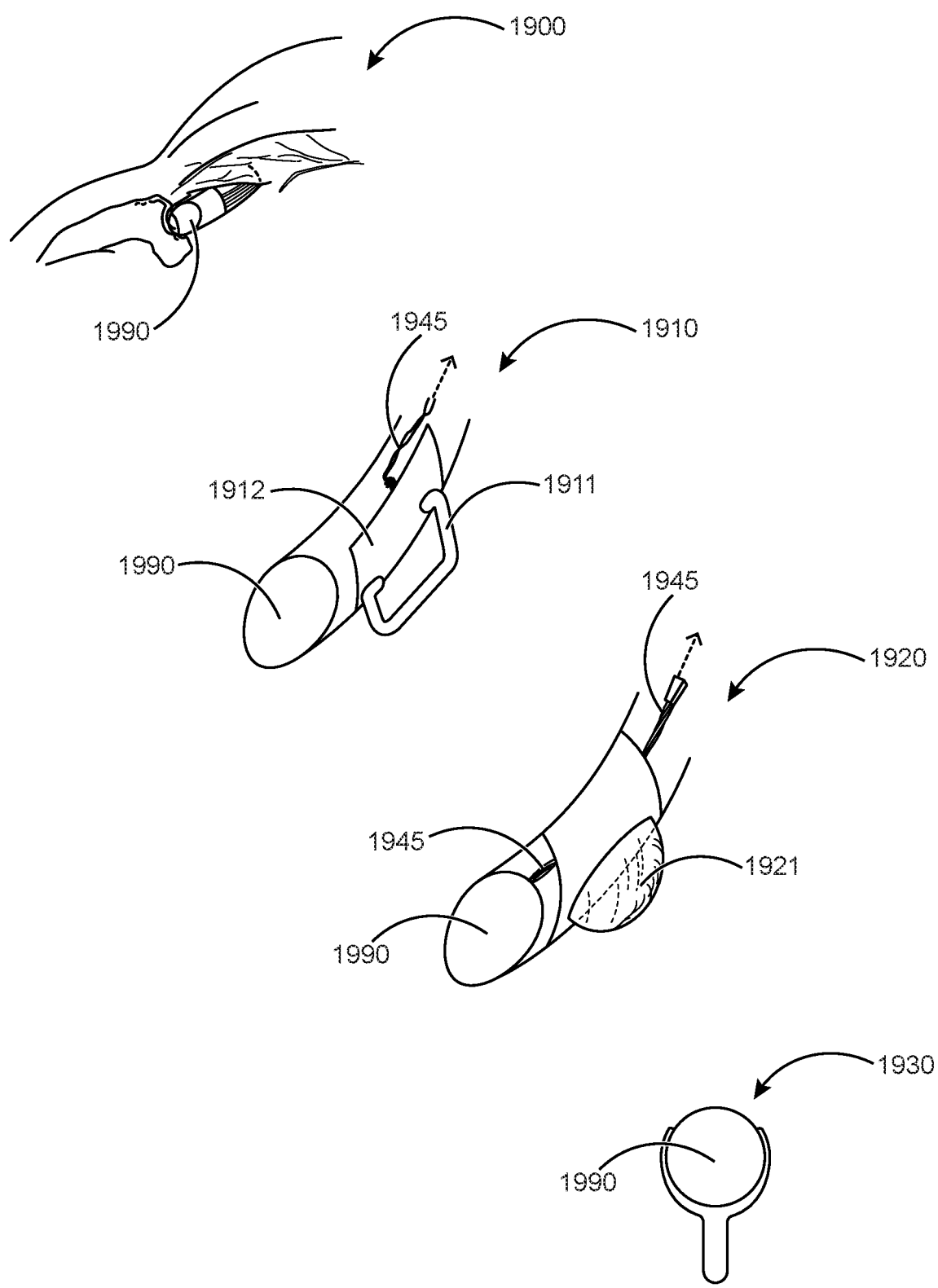
FIG. 19 shows perspective views of ciliary sulcus ring details as may be employed in embodiments.

FIG. 19 shows ciliary sulcus ring 1990 details as may be employed in embodiments. These details include projections, end connections, and continuous base connections as may be employed on or around a ciliary sulcus ring of embodiments. A sectional-view from within the eye of a portion of a sulcus ring is shown at 1900. 1910 shows a sulcus ring with a first sensor type while 1920 shows a sulcus ring with a second style of sensor. 1930 shows a cross-sectional end-view of an implanted sulcus ring.

To promote or obtain higher signal strength, it may be desirable to have projecting from the ciliary sulcus sensor ring, wire projections 1911 emanating from the conductive electrode surfaces 1912. However, if these are sharp projections, inflammation and scarring could result, even if the material is a biocompatible metallic material such as gold. The projections could be curved 1911, attaching at both ends of the aforementioned projections to the conductive surface of the sulcus ring sensor 1912, or alternatively, the entire base of the curved projection would connect to the sulcus ring sensor 1921. Then the projections would gently erode into the targeted tissue, enabling even better acquisition of the neuro-electrical signal. These projections would have a smooth, polished surface to ensure minimal inflammation, and would allow close apposition adjacent to and within the ciliary muscular tissue. A communication wire 1945 is also labeled.

Figure 20:
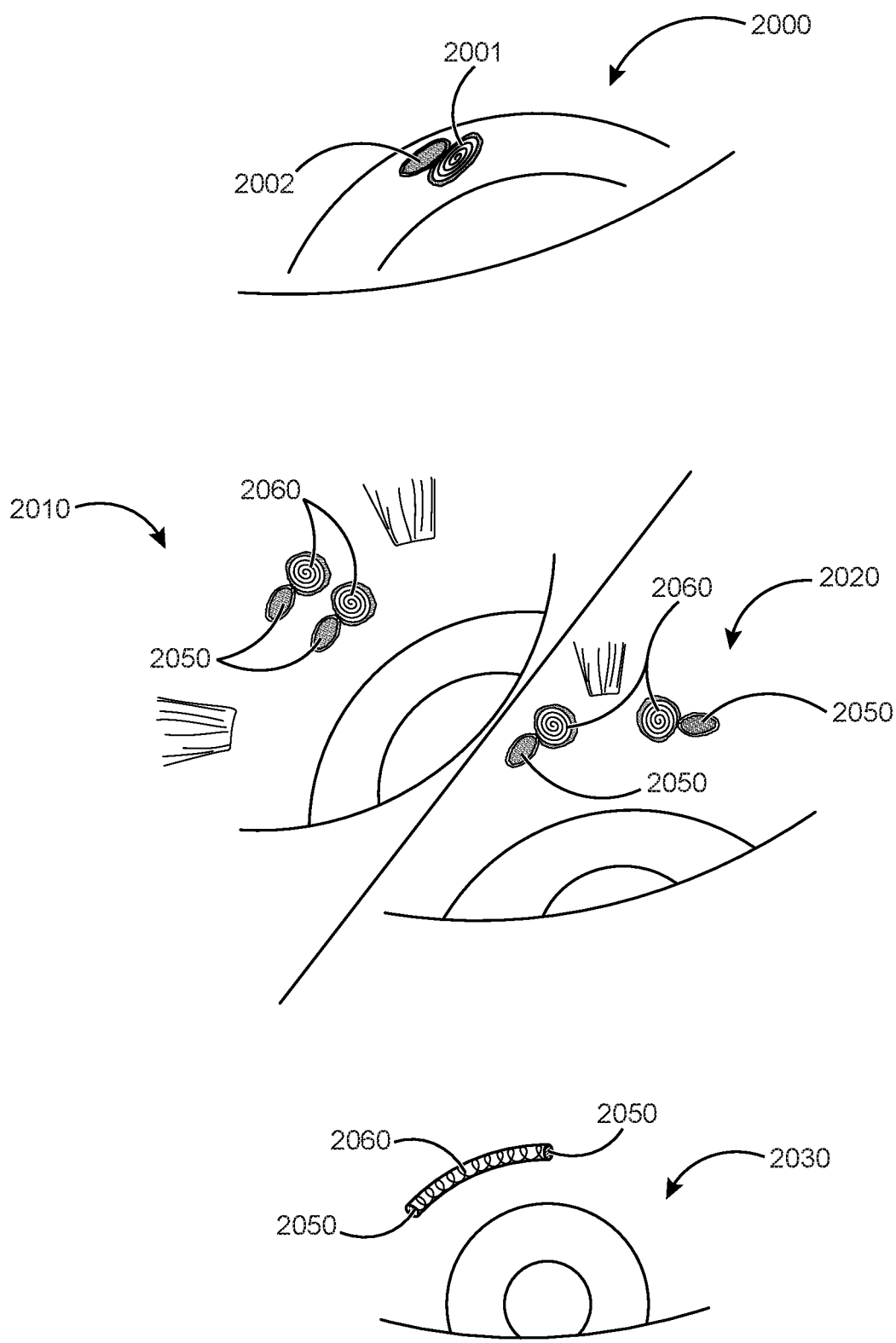
FIG. 20 shows various views of episcleral sensors as may be employed in embodiments.

FIG. 20 provides various views of episcleral sensors as may be employed in embodiments. These sensors include axial pairs overlying the ciliary muscle 2010, separated circumferential pairs 2020, or a continuous episcleral ring incorporating two or more sensors. In the case of episcleral sensors the sensor 2002 and RF coil 2001 could be implanted through a small incision in the conjunctiva/tenons capsule 2000. The episcleral sensor(s) may be positioned over the ciliary muscle, between 1 and 6 mm posterior to the corneal limbus, depending upon the individual's location of the CM as determined by VHF ultrasound imaging, alternative imaging methods such as MRI, or the surgeon's clinical judgement. The sensor may be implanted as pairs through the same incision, one of the sensors, such as the anode, posteriorly (2-6 mm posterior to the corneal limbus), and its mate, the cathode, anteriorly (1-3 mm posterior to the corneal limbus), or they may be implanted circumferentially in relation to each other, spaced from 2-8 mm apart, or 1-4 clock hours, in a fashion so as to avoid the external ocular structures such as muscles or vessels as shown at 2010. The distances of the electrodes may be calibrated so as to maximize the ciliary muscle accommodative signal. The circumferential electrodes could be positioned on a single, continuous semi-circular device for simple implantation through a single incision as shown at 2030. Other sensors 2050 and RF coils 2060 are labeled in FIG. 20 as well.

Figure 21:
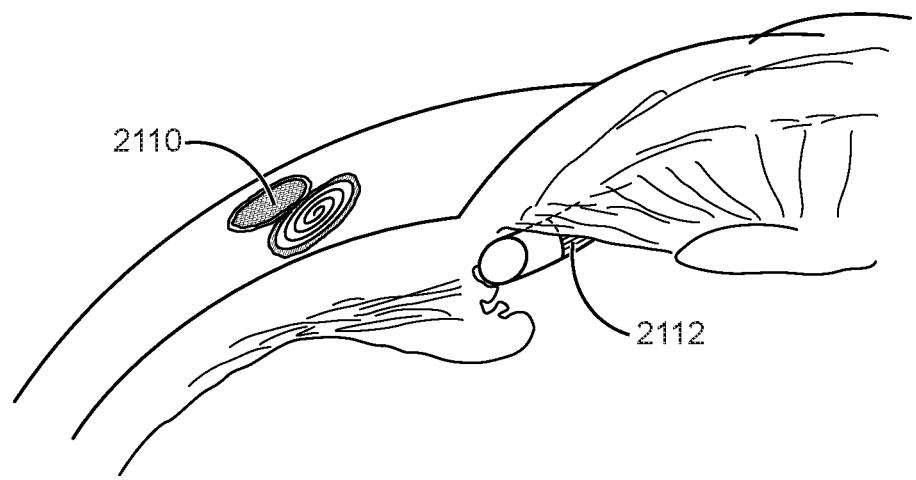
FIG. 21 shows a perspective view of implanted episcleral and ciliary sulcus sensors as may be employed in embodiments.

FIG. 21 shows an episcleral sensor 2110 paired with a ciliary sulcus ring sensor 2112 as may be employed in embodiments. In embodiments, an episcleral electrode sensor may be: paired with its sensor mate implanted in another location such as intraocularly; internal and adjacent to the ciliary muscle; within the ciliary sulcus; or with an intrascleral or suprachoroidal sensor. The paired sensor would ideally be approximately 1-4 mm distant from its mate.

Figure 22:
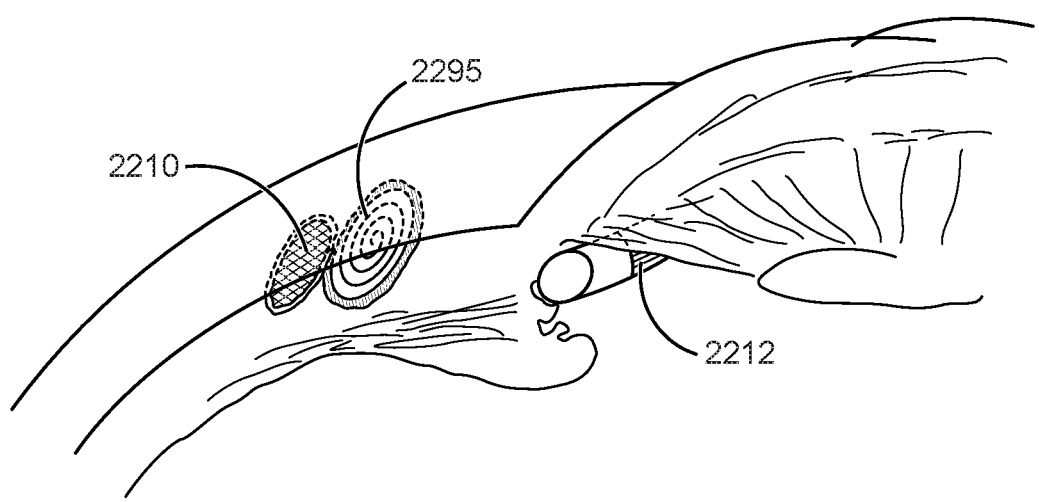
FIG. 22 shows a perspective view of a sensor and RF coil along with a ciliary sulcus sensor as may be employed in embodiments.

FIG. 22 shows an intrascleral sensor 2210 in a pocket as may be employed in embodiments. If one or a plurality of the paired sensor is implanted intrascleral, it could be implanted into a pocket tunneled into scleral tissue created surgically either with a trocar or some appropriate instrument. RF coil 2295 and ciliary sulcus sensor 2212 are also labeled in FIG. 22.

Figure 23:
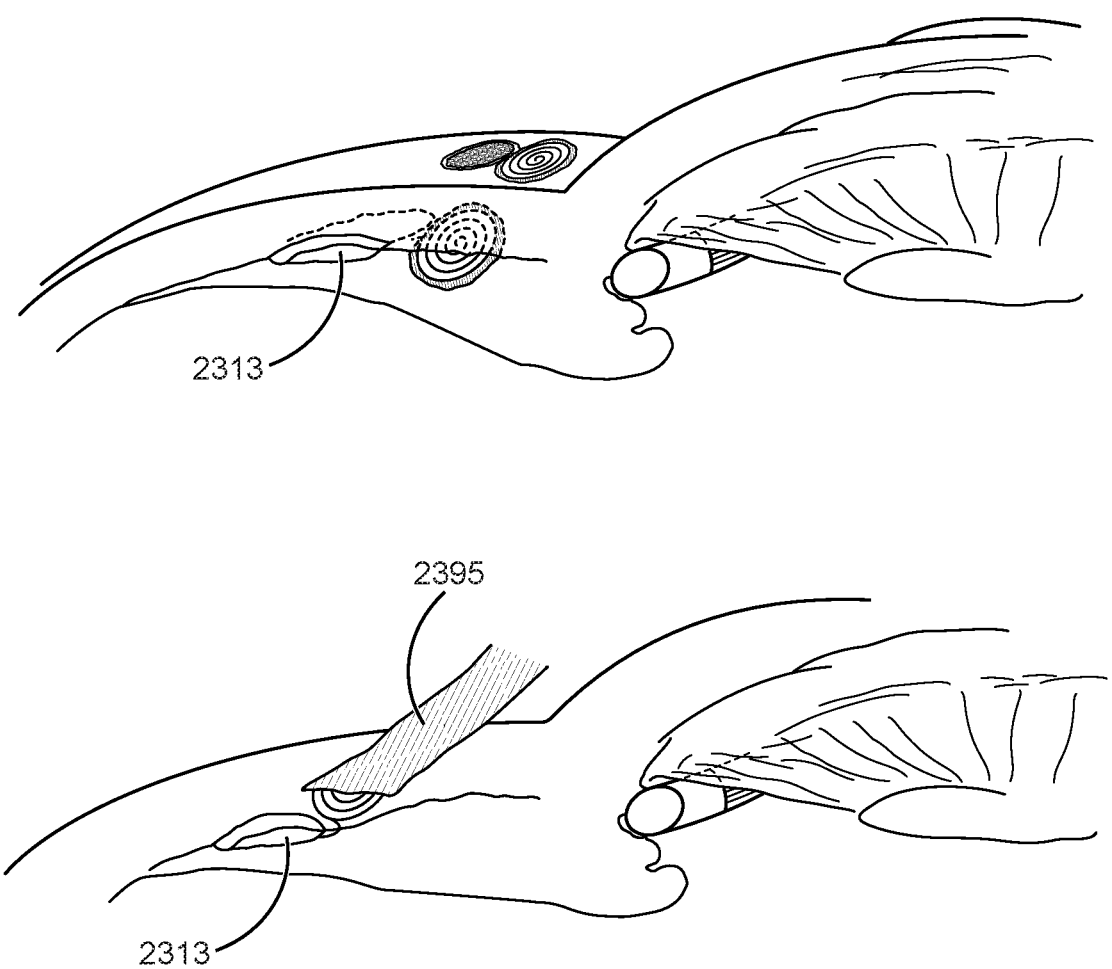
FIG. 23 shows a suprachoroidal sensor and an episcleral sensor, with trocar implantation as may be employed in embodiments.

FIG. 23 shows a suprachoroidal sensor 2313 and an episcleral sensor, with trocar 2395 implantation as may be employed in embodiments. The suprachoroidal sensor 2313 may be independent. If the sensors are positioned in the suprachoroidal space, one or more of projections emanating from an episcleral ring could be implanted by passing these either directly through sclera or by using a trocar 2395. Alternatively, the suprachoroidal electrode sensor 2313 may be independent of the episcleral sensor, but communicate with other components of the electrode system wirelessly using an attached radiofrequency coil.

Figure 24:
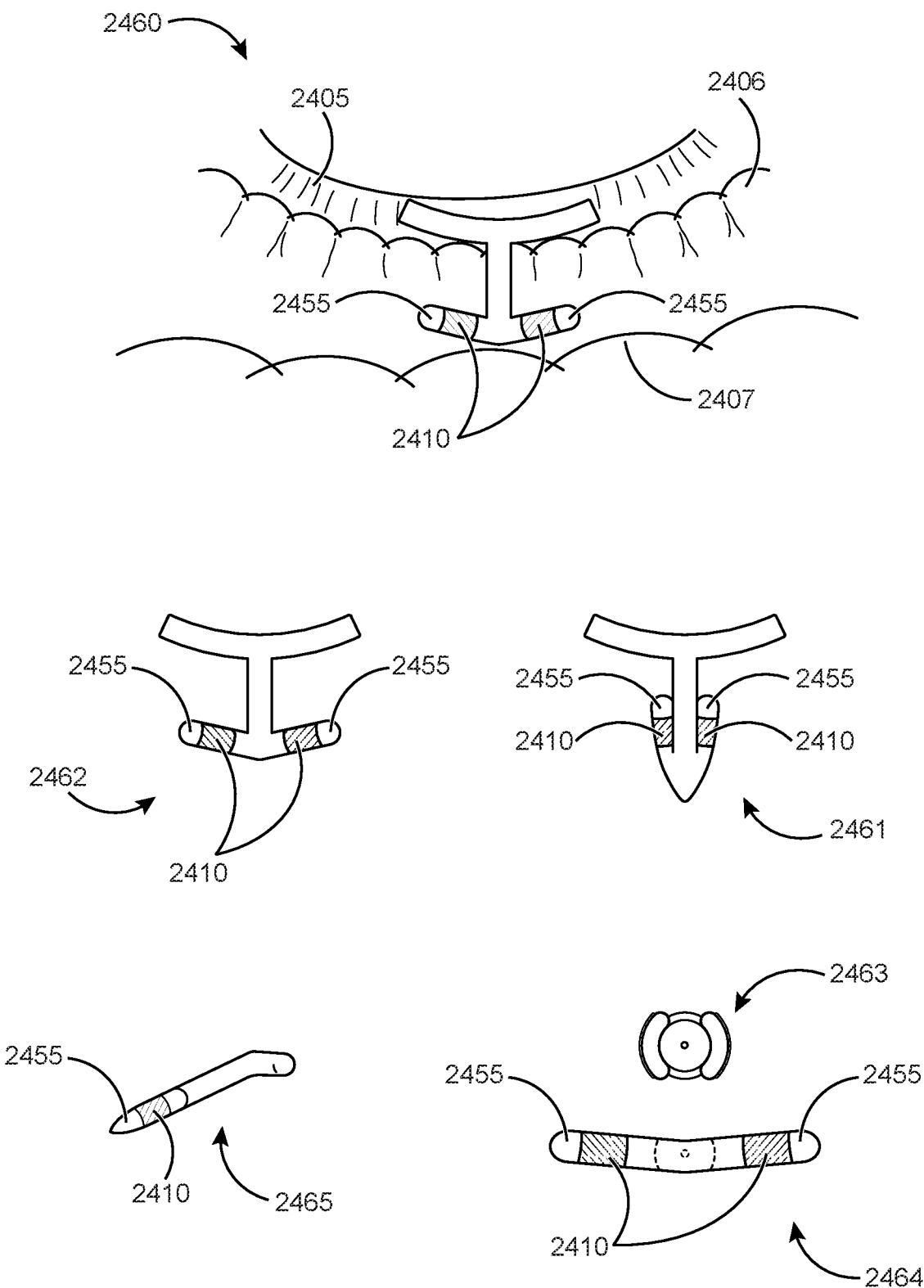
FIG. 24 shows intraocular/infrachoroidal sensors as well as particular tip details as may be employed in embodiments.

FIG. 24 shows ciliary sulcus 2405, ciliary process 2406, pars plana 2407, and intraocular/infrachoroidal sensors 2410 as well as particular tip details as may be employed in embodiments. If the sensors are positioned in the infrachoroidal or intraocular space adjacent or in apposition to the CM, one or more of electrode sensors may be passed through the zonules of the crystalline lens to reside adjacent to the internal surface of the choroid near the ciliary muscle. This sensor may preferably have a tip pointed or rounded so as to penetrate a resistant vitreous base, and could be comprised of a flexible Nitinol wire substrate, or silicone or PMMA substrate, and angulated with very mild compressive force to ensure its positioning adjacent to the ciliary muscle. The tip of the sensor could incorporate folding, retractable extensions 2455 to ensure contact with the CM.

All the possible locations and combinations of ciliary muscle electrode sensors are not listed here. Embodiments are not limited by the exact listed combinations as other locations combinations and designs and processes are also contemplated by and supported by the disclosure herein. Likewise, size of the various sensors, may be sized for insertion and implantation as described herein and the sensitivity may be sized to accommodate low voltage muscle action potentials. This size may be between 0.10 mm$^2$ and 8 mm$^2$, in various incremental steps of 0.1 mm$^2$ or more or less, depending upon sensor location.

Sensors in embodiments may include electrodes positioned for sensing ciliary muscle electrical activity. These electrodes may comprise various materials and may include metallic, biocompatible, material affixed to a biocompatible, flexible substrate. These sensors may be positioned adjacent to the CM for reception and transmission of ciliary muscle electrical activity and may use wired or wireless circuitry for communication to ASIC for processing for activation of an electro-active accommodating lens. These sensors and electrodes may be positioned in the ciliary sulcus, within the capsular bag, in the infrachoroidal space, in the suprachoroidal space, intrasclerally, and/or positioned in the episcleral space. The sensors may have curved smooth projections for protrusion and close apposition into the ciliary muscle tissue. The sensors may also be embedded within a contact lens where the conducting surface may be segmented as well as may be continuous along the implanted length of the sensor. The sensors may also have conducting surface continuous along the implanted length of the sensor and may comprise a radiofrequency coil or extension wire for communicating with other components. Battery power may also be used but it may also not be required for the sensors. These sensors may be sized 0.1 to 0.5 mm$^2$, 0.5 to 3.0 mm$^2$, 3.0 to 5.0 mm$^2$, and 5.0 to 8.0 mm$^2$, and may vary in shape, such as ovoid, circular, or rectangular according to the application in embodiments the electroactive lens may be an intraocular lens, a corneal inlay, a contact lens and a spectacle lens. In embodiments, sensors may be placed within the infrachoroidal space, suprachoroidal space, intrascleral tissue, within the episcleral/subconjunctival space, with or without a trocar.

As noted above, for example in conjunction with FIG. 13, embodiments may employ biologic impedance sensing as a process or in devices to detect electrical current changes across body tissues. Various types of testing are currently or have been performed, including Impedance Plethysmography for measuring blood flow and muscle function, Bioelectric Impedance Analysis for measuring body fat, and Impedance Cyclography for measuring ciliary muscle function in the eye.

In embodiments, recording electrodes can detect impedance changes in muscle with muscular activity. When impedance changes occur there is regularly a predictable relationship to the amplitude of an accommodative stimulus.

In embodiments, Impedance Cyclography may be employed. In so doing, a low voltage, high frequency alternating current may be passed near the ciliary muscle. Electrodes may be set up as a type of 4-terminal receptacle, or as a "Wenner" array. The Wenner electrode array consists of a line of four equally spaced electrodes. Current may be driven through the outer electrodes and potential may be measured between the inner electrodes. A complication of the electrode-tissue interface in a two electrode system is that variation in resistance may be recorded as a signal. In a four-electrode system, the contact resistances at all four electrode-tissue interfaces may be assumed equal. Since the contact resistances of the two driving and two sensing electrodes are equal, the output of the impedance circuit is the potential difference between the two sets of electrodes, contact resistances cancel, and only the variation in internal resistance remains. Also, any disruption or imbalance of electrical contact at the electrode-tissue interface results in a gross change in the impedance output and could be compensated for by the operator.

Impedance Cyclography applications can be employed in embodiments where a 0.2 milliampere 50 kHz sinusoidally alternating constant current may be passed near the vicinity of the ciliary muscle with electrodes embedded in a contact lens. The 0.2 milliampere current can be sufficient to allow a stable current flow but not enough to affect the eye nor to be felt by the subject. The 50 kHz frequency may be used because, without being bound by theory, it is believed the inductive and capacitive components of impedance are minimized or near minimized at this frequency and the impedance is, for cyclographic purposes, directly proportional to the resistive component.

In use, variation in tissue resistance can modulate a 50 kHz carrier wave, or carrier wave from 25 kHz to 150 kHz, from a driving electrode, and this modulated carrier wave may be received by the sensing electrodes. The potential difference between the sensing electrodes, caused by the alternating current field which is produced by the driving electrodes, may be amplified in embodiments. This signal and the compensation signal (the unmodulated carrier wave) can undergo rectification and filtration in embodiments and may then be effectively subtracted one from the other in embodiments. In the case of certain Impedance Cyclography, the output may be amplified in embodiments before being recorded for analysis. In embodiments, the amplified output may be fed into an Application Specific Integrated Circuit (ASIC) of embodiments in order to trigger an electro-active lens or lens system of various types, whether intra-ocular or extraocular. In embodiments, if the current is held constant, the circuit output (potential variation) may be directly proportional to the change in impedance as described by Ohm's law, and if the detected change in impedance is linear or even variable depending upon accommodation, this output could be used to drive a tunable Electro-Active lens.

Thus, in embodiments, a form of Impedance Cyclography may be used to detect accommodative activity of the ciliary muscle, and then use the impedance change signal, modulated and controlled by an ASIC, to activate an electro-active accommodative lens, whether this lens is located within or on the eye, or external to the eye such as in contact lens or spectacles. Other components may also be modified or adjusted or controlled in this fashion as well.

In embodiments, a device to measure the impedance change, an impedance sensor system, may include conductive, metallic electrodes. They may be positioned within a contact lens. A preferred embodiment may include electrodes that are composed of a biocompatible, conductive metal, such as gold or silver, or conductive metal with biocompatible coating, located close to the ciliary muscle, preferably within 3 mm, either positioned in the episcleral location, intrascleral, suprachoroidal adjacent to the muscle, in the ciliary sulcus, or in the intracapsular bag.

Embodiments may also relate to modifications of devices that cause a change in the shape of a compressible, accommodating intra-ocular lens (TOL), which have previously been implanted to replace the original crystalline lens of a subject, and which typically includes an internal deformable lens having an external membrane. The IOL can be electronically coupled to a sensor, such as an electromyographic (EMG) receiver (or a series of EMG receivers) implanted in or near the ciliary muscle within the eye. One or more EMG receivers may serve to detect a signal created by the ciliary muscle. In embodiments, the sensor, such as an EMG receiver, can transmit the ciliary muscle signal to a signal processor such as a transducer or microprocessor which generates an electrical signal. The transducer can then send the resultant electrical signal to an IOL system that includes an annular support ring system acting as an electrostrictive/piezoelectric actuator that creates a force of contraction that acts on the IOL. In embodiments, the piezoelectric actuator may be in the form of a flexible, encircling tube made of an electro-active polymer or other piezoelectric material (also termed herein as an inner annular ring of the annular support ring system). The force of contraction created by the piezoelectric actuator can mimic that created by the ciliary muscle onto a native lens, thereby causing a shape change in the IOL.

As noted, embodiments may provide for an accommodative intra-ocular lens (IOL) system, comprising: (a) a compressible accommodating IOL; (b) an external lens membrane; (c) an annular support ring system adapted for implantation in the human eye, the annular support ring system comprising an outer annular ring and an inner annular ring, the outer annular ring being rigid for resisting compressive forces of the native capsular bag, the inner annular ring encircling the external lens membrane and formed of an electro-active material; and (d) a transducer in electrical communication with the inner annular ring for application of an electric field thereto, wherein the transducer is configured for mechanical coupling with the ciliary muscle when the system is implanted in the eye such that the transducer can modulate the electric field it applies to the inner annular ring in response to ciliary muscle movements to cause a change in shape of the IOL so as to facilitate accommodation.

Embodiments can also provide for a device for causing a change in focal length of an accommodating intra-ocular lens (TOL) of a subject, the device comprising: (a) an IOL system comprising a changeable accommodating IOL, an external lens membrane, and an annular support ring system for providing a means to cause a change in focus of the IOL, the annular support ring system comprising two concentric rings including an outer annular ring and an inner annular ring, the outer annular ring being rigid for resisting compressive forces of the native capsular bag, the inner annular ring encircling the external lens membrane and being made of an electro-active polymer; (b) at least one sensor for detecting a signal from the subject's ciliary muscle; (c) a signal processor for receiving and processing the ciliary muscle signal to generate a corresponding electrical signal; and (d) a transducer for transmitting the electrical signal to the inner annular ring of the IOL system, wherein the inner annular ring is activated upon receiving the electrical signal from the transducer, activation of the inner annular ring causing an accommodative change in shape of the IOL.

Embodiments may also provide for methods for causing a change in shape of a compressible, accommodating intra-ocular lens (TOL) in a subject, the method comprising steps such as: (a) implanting at least one sensor for detecting a signal from a subject's ciliary muscle into an eye of the subject; (b) detecting a ciliary muscle signal with the at least one sensor; (c) transforming the ciliary muscle signal into an electrical signal; and (d) transmitting the electrical signal to an implanted IOL system, wherein the transmitted electrical signal causes an electro-active element encircling the IOL to constrict and cause a change in shape of the IOL.

Polymer artificial muscle technologies may be employed in embodiments to produce strains and stresses using electrostatic forces, electrostriction, ion insertion, and molecular conformational changes in embodiments. Materials used may include electro-active polymers, elastomers, ionically conducting polymers, and carbon nanotubes. Some polymer actuators may be preferred when they exceed that of natural muscle in many respects, making them particularly attractive for use wherever a muscle-like response is desirable, including in medical devices, prostheses, robotics, toys, camera lenses, and biomimetic devices.

As illustrated in FIGS. 2 and 25-28, a synthetic IOL 15 for possible use with embodiments replaces the natural crystalline lens 14. The IOL can be part of an IOL system, which can include an internal compressible accommodating IOL 15 which incorporates a flexible, elastic external lens membrane 15a about its periphery, and an annular support ring system 40. The annular support ring system provides a means to cause a change in shape of the IOL. The annular support ring system typically consists of two (2) concentric, adjacent encircling elements: an outer annular support ring 40a and an adjacent inner annular support ring 40b. The inner annular ring 40b encircles, and is attached to, the external lens membrane 15a, which encases the IOL 15. The IOL 15, external lens membrane 15a and the annular support ring system 40a, 40b are all positioned within the native capsular bag 22, which previously encased the (now removed) natural crystalline lens 14. The capsular bag 22 and it's supporting zonular ligaments 26 serve as a support structure for the IOL system and the annular support ring system.

Figure 25:
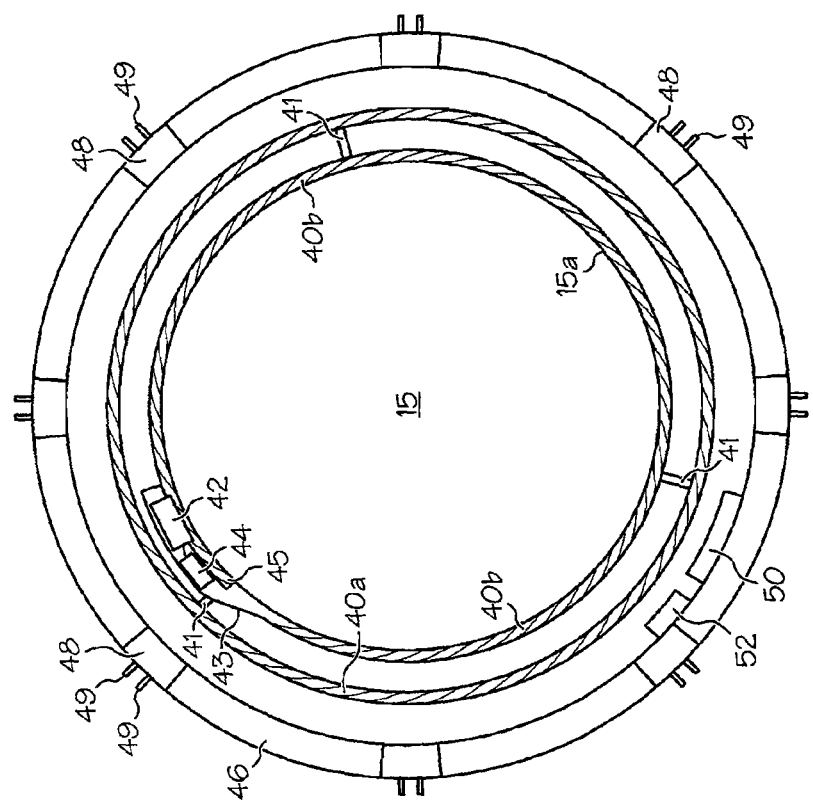
FIG. 25 is a perspective frontal view of a system as may be employed in embodiments.
Figure 26:
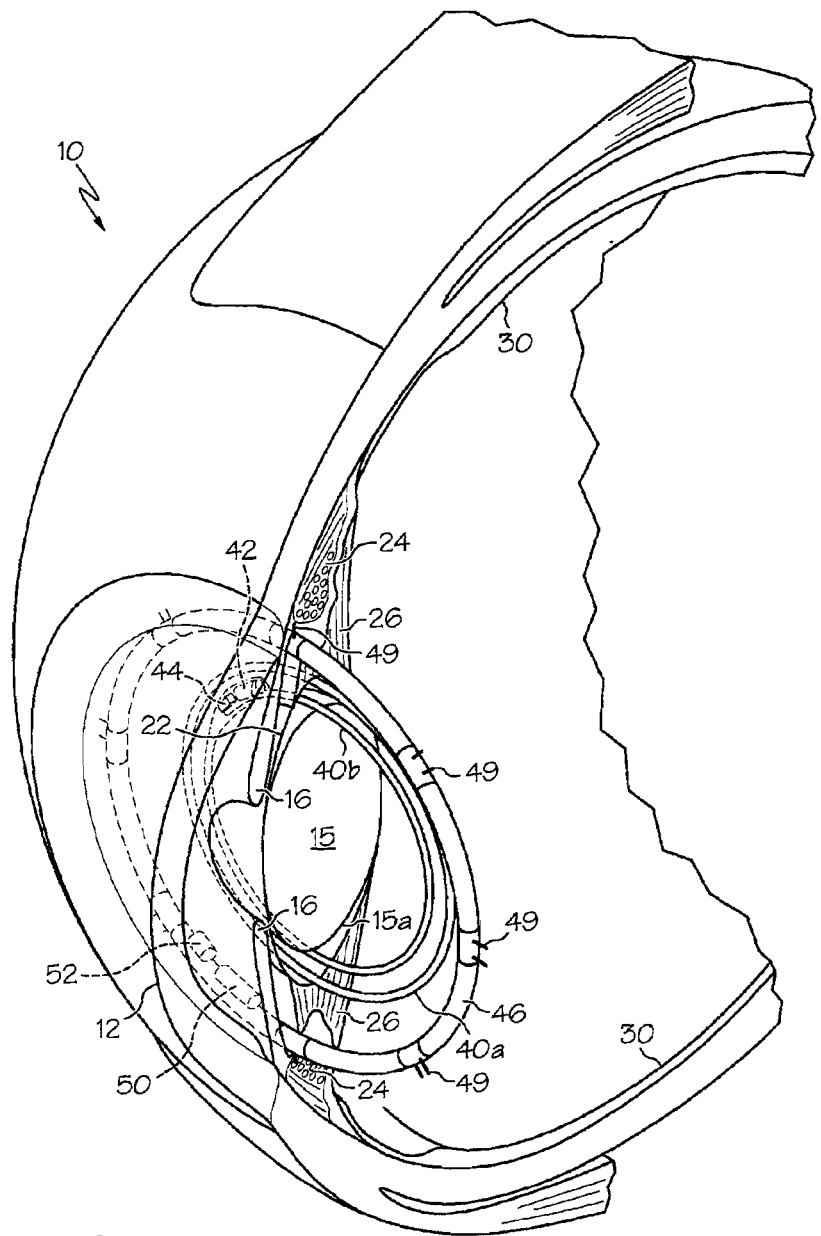
FIG. 26 is a partial cross-sectional view of the human eye showing the system of FIG. 25 after implantation into the eye as may be employed in embodiments.

As illustrated in FIG. 25 the inner annular support ring 40b encircles the external lens membrane 15a and compresses or tightens around the IOL 15 in response to an applied electric field, which results in a change in shape or other change in focal length of the IOL 15. To accomplish compression, the inner annular ring 40b may be flexible and an encircling tube formed of an electro-active polymer or a piezoelectric material. The inner annular ring 40b may be formed of a core portion made of a non-electro-active, yet biocompatible material and include a layer of an electro-active/piezoelectric material disposed on its surface.

Piezoelectricity is the ability of certain solid materials to convert mechanical energy into electrical energy, and vice versa. The direct piezoelectric effect is the generation of an electric charge proportional to an applied mechanical stress. Piezoelectric sensors, like acceleration sensors and pressure sensors, exploit the direct piezoelectric effect. The reverse piezoelectric effect is that these same materials become mechanically stressed (deformed in shape) when a voltage is applied, the deformation again being proportional to the applied field. An example of the use of the reverse effect is found in piezoelectric actuators. The piezoelectric compression plate 1463 of FIG. 14, and the inner annular ring 40b of the present invention is an example of a piezoelectric actuator.

In addition to materials such as crystals, ceramics, and biological matter like bones, tendons and teeth, a number of polymeric materials exhibit strong piezoelectric effects. Polyvinylidene fluoride (PVDF) is a particularly well known example, as are its copolymers with hexafluoropropylene (PVDF-HFP) or trifluoroethylene (PVDF-TrFE). PVDF is sometimes called an electro-active polymer, or EAP. Other EAP's can include an electrically activated graphene, or gel encased in a biocompatible outer membrane.

As noted above, the inner annular ring 40b of FIG. 25 can be made of an EAP such as PVDF or the like, or the ring 40b can have a core portion made of a non-electro-active, yet biocompatible material, with a surface layer of electro-active/piezoelectric material disposed thereon. The inner ring 40b may be generally placed contiguous with the external lens membrane 15a, which encases the IOL 15, to allow it to perform a constricting function on the IOL. Thus the inner ring 40b, when activated by an electrical signal, causes a constricting, compressive movement against the IOL 15.

A ciliary sulcus ring 46, which can be implanted in the ciliary sulcus 32 via intra-ocular endosurgery (now commonly and easily performed in a procedure called endocyclophotocoagulation), can communicate with the inner annular support ring 40b via a transducer 50. The ciliary sulcus ring 46 supports at least one and typically a series of ciliary muscle signal sensors 48, illustrated here in the form of electromyographic (EMG) receivers for detecting ciliary muscle contraction. Each EMG receiver 48 can include contacts or miniaturized electrodes in the form of ciliary muscle probes 49, typically in pairs, for entering the ciliary muscle 24 (FIG. 3). However, embodiments can employ sensors known in the art that can detect a ciliary muscle signal by electrical/neuroelectrical means, chemical/neurochemical means, mechanical movement of the ciliary muscle, or a combination of these means.

The ciliary muscle signal sensors can be in the form of piezoelectric sensors, a first sensor positioned within the ciliary sulcus, typically on the ciliary sulcus ring 46, and a companion sensor positioned on the outer annular support ring 40a. Movement of the first sensor relative to the companion sensor due to a piezoelectric effect provides the ability to detect ciliary muscle movement in response to the accommodative reflex. Further, a series of ciliary muscle sensors can be supported on both the ciliary sulcus ring 46 and the outer annular support ring 40a, and the degree of movement of these sensors relative to one another can provide very sensitive means for detecting an accommodative signal from the ciliary muscle. Furthermore, the ciliary muscle signal sensors could be implanted external to the ciliary muscle, incorporated into the outer annular support ring 40a, within the capsular bag, subsclerally between sclera and ciliary muscle, intrasclerally within a surgically fashioned pocket, in the subconjunctival/episcleral space, or even within a large diameter contact lens.

Activation of electro-active polymer material of the inner annular ring 40b causes the ring 40b to tighten, thereby shortening in both circumference and diameter and exerting a compressive force on the IOL 15 to change the IOL shape. The outer annular support ring 40*a* can typically be manufactured of a non-electro-active/piezoelectric material, and is typically more rigid and adapted to resist compressive, fibrotic contraction forces of the native capsular bag 22. Also, the outer annular ring 40*a* can include attachments of optical, electrical or magnetic sensors (not shown) with corresponding sensors/receivers located on the ciliary sulcus ring 46. The sensors on the ciliary sulcus ring 46 and the outer annular ring 40*a* would allow detection of the ciliary muscle action by the relative movement of the two components (40*a*, 46) during accommodation.

As noted above, modern cataract surgery typically involves removing the natural lens while leaving the clear native capsular bag 22 to hold the new intraocular lens in place. The capsule 22 that remains has epithelial cells on it which can continue to produce lens fibers. These fibers cannot be laid down in an organized manner and will form little beads or "pearls" on the lens capsule 22, forming a secondary membrane. When these pearls accumulate in the pupil, they cause a blurring of vision similar to that experienced with a cataract. This occurs approximately 30-40% of the time and can appear at any time after cataract surgery, even as much as five or more years later.

Thus, there is a risk that the surrounding capsular bag 22 will scar down, bind, compress, contract, or otherwise reduce the effectiveness of a single annular ring. This may be avoided or its risk reduced by employing the double ring system as disclosed herein, which includes the outer annular support ring 40*a* and the inner annular support ring 40*b* of embodiments of the present invention. With this double annular support ring configuration, the outer annular support ring 40*a* can protect the inner annular support ring 40*b* from the contractile forces of a fibrotic capsular bag 22. For example, in FIG. 25 the outer ring 40*a* is attached to the inner ring 40*b* by attachments 41 at intervals along their lengths as shown, as needed for stability, such as every one-third to one-fourth of the way around their circumference. The attachments 41 between the outer ring 40*a* and the inner ring 40*b* may likely be via mini-welds or clips.

Since the inner ring 40*b* is comprised of (or includes a surface layer of) an electro-active/electrostrictive material (such as PVDF), a change in shape such as compression of this flexible, encircling tube around the IOL can be adequate to cause a compressive force exerted on the IOL. Alternatively, the inner ring 40*b* can be in the form of a hollow tube that includes a free or distal end (not shown) that can fit within a proximal end that may allow the ring to slide within itself. Regarding such a tubular embodiment, the ring can be a tapered tube in which the circumference of the sliding end is smaller than the opposite end of the ring, so that the sliding, smaller end can fit inside the larger, stationary end as it slides; alternatively, the sliding end can be larger than the other end of the ring, so that the sliding end can envelop the stationary end as it slides. Such sliding of the inner ring within itself may further decrease both the diameter and circumference of the inner ring 40*b*, resulting in a larger compressive force being exerted upon the IOL. With such a sliding ring embodiment, however, it should be noted that the inner ring could not have a connection or attachment 41 at its sliding distal end because it would not be able to slide into its proximal end.

Not only can the outer ring 40*a* shown in FIGS. 25-28 provide rigidity to the inner ring 40*b* in the face of scarring of the lens capsular bag 22, thereby protecting the inner ring, but as noted above it can also include sensors for detecting relative motion of the ciliary sulcus ring 46. This will allow detection of ciliary muscle action by the relative movement of the two components (40*a*, 46) during accommodation. In this manner, a first sensor (or series of sensors) can be positioned on the ciliary sulcus ring 46, and a companion sensor (or series of sensors) can be located on the outer annular support ring 40*a*, in order to detect relative motion of the ciliary sulcus ring 46 following ciliary muscle movement. Companion sensors can also be placed on the iris 16 or other ocular tissue.

The ciliary muscle sensors 48 can be either flat, or tubular areas contiguous with the main body of the ciliary sulcus ring 46, and can provide electrical, mechanical or chemical recognition of a ciliary muscle signal via miniaturized electrode probes or contacts 49. An ASIC (Application Specific Integrated Circuit) 52 can be included to act as a signal processor to modulate the ciliary muscle signal detected by the sensor 48, converting it to an electrical signal that can then be sent to the inner annular ring 40*b* via the transducer 50. Typically, a single ASIC system is needed for a ciliary sulcus ring 46; however, in embodiments another set may be attached as backup in case of a failure of one of the components. The transducer 50 can be directly wired to the inner annular ring 40*b*, or it can work via radio frequency (RF) transmission or other wireless system known in the art. Regardless of the means of transmission, communication of the ciliary muscle signal from the sensors 48 to the inner annular ring 40*b* creates a change in shape of the inner annular ring 40*b*, resulting in compression of the IOL 15.

As noted above, the ciliary muscle sensor 48 can be a myoelectrical sensor such as an EMG receiver known in the art for detecting muscle action potentials for taking clinical EMG measurements. With EMG-type sensors, miniaturized electrode probes or contacts 49 may be incorporated onto the ciliary sulcus ring 46 and implanted into the ciliary muscle via intra-ocular endosurgery (i.e. via endocyclophotocoagulation). Various EMG electrodes or probes may be used as a sensor supported on the ciliary sulcus ring of embodiments.

The ciliary sulcus ring 46 is a generally circular ring which is implanted into the ciliary sulcus 32 of a subject. The ciliary sulcus ring 46 may be made of polymethylmethacrylate, with or without a collamer coating, or a combination of biocompatible metals having conductive plates. If the ciliary sulcus ring 46 includes such conducting plates, the plates can serve as the sensors/EMG contacts 48, and may include fine wire appendages as probes 49 for entering the ciliary muscle. The composition of the probes 49 should be a metal material or an alloy that is both biocompatible and conductive. An alternative method is to incorporate the EMG sensor or electrode into the structure of the outer annular ring 40*a* which is implanted into the capsular bag. These would preferably function as surface electrodes. The sensitivity and orientation of these sensors placed within the outer annular ring 40*a* would be such that directional filtering would facilitate electromyographic detection.

While embodiments have been illustrated herein, it is not intended to restrict or limit the scope of the appended claims to such detail. Additional advantages and modifications will be readily apparent to those having ordinary skill in the art. Accordingly, changes may be made to the above embodiments without departing from the scope of the invention.

What is claimed is:
1. An electro-active intraocular lens comprising:
   an adjustable intraocular lens;
   a plurality of sensor arms extending away from the adjustable intraocular lens, each of the arms comprising a pair of electric sensors, the pair of electric sensors comprising a driving electrode and a sensing electrode; and a processor configured to receive EMG signals sensed by sensing electrodes of the plurality of sensor arms, and to control focus of the adjustable intraocular lens using the received EMG signals.

2. The electro-active intraocular lens of claim 1 wherein the sensor arms have a parabolic or conchoidal shape and are positioned to center the intraocular lens within the capsular bag when the adjustable intraocular lens is implanted in an eye of a user of the adjustable intraocular lens.

3. The electro-active intraocular lens of claim 1 wherein the adjustable intraocular lens is detachable and wherein the at least one pair of electric sensors are part of a wenner electrode array.

4. The electro-active intraocular lens of claim 1 wherein at least one of the electric sensors is positioned on a sensor arm such that when the adjustable intraocular lens is implanted in an eye of a user of the adjustable intraocular lens, the sensor is positioned in an intravitreal space.

5. The electro-active intra-ocular lens of claim 1 wherein the processor carries out steps comprising detecting the EMG signals, determining the need for accommodative correction based on the detected signals, providing a drive signal to affect a change in the adjustable intraocular lens, which at least partially restore lost accommodation of an eye of a user of the adjustable intraocular lens.

6. The electro-active intra-ocular lens of claim 1 wherein the processor determines impedance of a received physiological signal impedance cyclography and signals received from one or more of the electric sensors.

7. An ocular system for improving vision comprising:
an adjustable intraocular lens;
a pair of haptic sensor arms extending away from the adjustable intraocular lens, each of the arms comprising a mated pair of electric sensors, the mated pair of electric sensors comprising an anode sensor and a cathode sensor; and
a processor configured to receive EMG signals sensed by the anode sensors and the cathode sensors and to control focus of the adjustable intraocular lens using the received EMG signals.

8. The system of claim 7 wherein at least one mated pair of electric sensors are positioned and configured to detect at least impedance changes occurring in a ciliary muscle during accommodation.

9. The system of claim 8 wherein the impedance changes are used as input for the adjustable intraocular lens and wherein the adjustable intraocular lens is a variable focus lens.

10. The system of claim 7 further comprising an electric sensor sized between 0.5 mm$^2$ and 8.0 mm$^2$, and configured to be implanted in at least one of the following ocular locations of a user of the adjustable intraocular lens: the episcleral, the intrascleral, the suprachoroidal adjacent to the ciliary muscle, the ciliary sulcus, the intracapsular bag, or the infrachoroidal of the user of the adjustable intraocular lens.

11. The system of claim 7 wherein the at least one pair of electric sensors is configured to wirelessly transmit a received signal to the processor and wherein the pair of haptic sensor arms is sized to fit within a capsular bag of a user of the adjustable intraocular lens.

12. The system of claim 7 wherein the at least one pair of electric sensors has protrusions configured for positioning about the ciliary muscle of a user of the adjustable intraocular lens and wherein each of the haptic sensor arms further comprises a reference sensor, the reference sensor configured to detect a reference signal level for comparison by the processor.

13. The system of claim 7 wherein the processor controls focus of the adjustable intraocular lens by using accommodative spike amplitude and resting spike amplitude of a ciliary muscle signal as well as accommodative spike frequency and resting spike frequency of a ciliary muscle signal.

14. The system of claim 7 wherein the processor is further configured to run instructions stored on a memory, the instructions causing the processor to control operation of the adjustable intraocular lens and instruct the adjustable intraocular lens to focus an optic of the adjustable intraocular lens, in order to correct vision for a user of the adjustable intraocular lens, using the received EMG signals wherein the adjustable intraocular lens provides active near focus for an eye of the user of the adjustable intraocular lens.

15. The system of claim 14 wherein the processor is also configured to run instructions to separate a received non-accommodative, resting signal from an accommodative, active signal.

16. The system of claim 14 wherein focus of the optic of the adjustable intraocular lens is continuously variable.

17. The system of claim 14 wherein the processor is also configured to run instructions to separate low voltage, low amplitude received signals (10-79 µV) from higher voltage, higher amplitude received signals (80-250 µV).

18. The system of claim 14 wherein the processor is also configured to run instructions that separate low frequency spike trains (0-1/100 msec, 1-2/100 msec, 3-4/100 msec) from high frequency spike trains (5-10/100 msec).

19. The system of claim 7 wherein at least two of the electric sensors are tuned to receive EMG signals between the range of 10 microvolts (µV) and 250 microvolts (µV).

* * * * *